US006301964B1

(12) United States Patent (10) Patent No.: US 6,301,964 B1
Fyfe et al. (45) Date of Patent: *Oct. 16, 2001

(54) MOTION ANALYSIS SYSTEM

(75) Inventors: Kenneth R. Fyfe, Edmonton; James K. Rooney; Kipling W. Fyfe, both of Cochrane, all of (CA)

(73) Assignee: DyhaStream Innovations Inc., Cochrane (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/347,305

(22) Filed: Jul. 6, 1999

Related U.S. Application Data

(63) Continuation-in-part of application No. 08/949,472, filed on Oct. 14, 1997, now Pat. No. 5,955,667.

(51) Int. Cl.[7] .................................................. G01P 15/08
(52) U.S. Cl. .......................... 73/510; 73/865.4; 702/160
(58) Field of Search ............................. 73/490, 492, 489, 73/865.4, 510; 702/141, 160, 166

(56) References Cited

U.S. PATENT DOCUMENTS

| 3,797,010 | 3/1974 | Alder et al. . |
| 4,371,945 | 2/1983 | Karr et al. . |

(List continued on next page.)

FOREIGN PATENT DOCUMENTS

| 42 22 373 A1 | 1/1994 | (DE) . |
| 862074 | 9/1981 | (RU) . |
| 885897 | 11/1981 | (RU) . |
| WO 97/24582 A1 | 7/1997 | (WO) . |
| WO 99/44016 A1 | 9/1999 | (WO) . |

OTHER PUBLICATIONS

J.R. W. Morris, "Accelerometry—A Technique for the Measurement of Human Body Movements", J. Biomechanics, 1973, vol. 6, Pergamon Press, Great Britain, pp. 729–736.
N.K. Mital, "Computation of Rigid–Body Rotation in Three–Dimensional Space From Body–Fixed Linear Acceleration Measurements", Journal of Applied Mechanics, Dec. 1979, vol. 46, pp. 925–930.

(List continued on next page.)

*Primary Examiner*—Helen Kwok
(74) *Attorney, Agent, or Firm*—Cesari and McKenna, LLP

(57) ABSTRACT

A device comprised of at least a pair of accelerometers and a tilt sensor mounted in fixed relation to a datum plane defining surface (sole of a shoe) may be used for extracting kinematic variables including linear and rotational acceleration, velocity and position. These variables may be resolved into a selected direction thereby permitting both relative and absolute kinematic quantities to be determined. The acceleration is determined using a small cluster of two mutually perpendicular accelerometers mounted on a shoe. Angular orientation of the foot may be determined by double integration of the foot's angular acceleration (which requires a third accelerometer substantially parallel to one of the two orthogonal accelerometers). The two orthogonal accelerations are then resolved into a net horizontal acceleration or other selected direction which may be integrated to find the foot velocity in the selected direction. The average of the foot velocity corresponds to the subject's gait speed.

50 Claims, 24 Drawing Sheets

U.S. PATENT DOCUMENTS

| | | |
|---|---|---|
| 4,578,769 | 3/1986 | Frederick . |
| 4,736,312 | 4/1988 | Dassler et al. . |
| 4,768,152 | 8/1988 | Egli et al. . |
| 4,917,105 * | 4/1990 | Tiitola et al. ........................ 128/779 |
| 5,097,706 | 3/1992 | LeNouvel et al. . |
| 5,341,819 * | 8/1994 | Hyvarinen ........................... 128/779 |
| 5,524,637 | 6/1996 | Erickson . |
| 5,583,776 | 12/1996 | Levi et al. . |
| 5,724,265 | 3/1998 | Hutchings . |
| 5,899,963 | 5/1999 | Hutchings . |
| 5,955,667 * | 9/1999 | Fyfe ....................................... 73/490 |
| 6,073,086 | 6/2000 | Marinelli . |
| 6,122,960 | 9/2000 | Hutchings et al. . |

OTHER PUBLICATIONS

Rex T. Shea, "Computing Body Segment Trajectories in Hybrid III Dummy Using Linear Accelerometer Data", Journal of Biomechanical Engineering, Feb. 1994, vol. 116, pp. 37–43.

W.C. Hayes, "Leg Motion Analysis During Gait by Multi-axial Accelerometry: Theoretical Foundations and Preliminary Validations", Journal of Biomechanical Engineering, Aug. 1983, vol. 105, pp. 283–289.

M. Macomber, "Some Operational Aspects of Inertial Surveying Systems", pp. 377–382.

Mario A LaFortune, "Three–Dimensional Acceleration of the Tibia During Walking and Running", Journal of Biomechanics, vol. 24, No. 10, 1991, Pergamon Press, Great Britain, pp. 877–886.

Nusholtz, "Geometric Methods in Determining Rigid–Body Dynamics", Experimental Dynamics, Jun. 1993.

Aminian et al., "Estimation of Speed & Incline of Walking Using Neutral Networks", IEEE Transactions on Instrumentation & Measurement, vol. 44, No. 3, Jun. 1995.

* cited by examiner

Tangential
Acceleration

Normal
Acceleration

Foot Tilt
Angle

Horizontal
Acceleration

Horizontal
Foot Velocity

Mean Speed
of Travel angular acceleration
or angular velocity

MOTION ANALYSIS SYSTEM

CROSS REFERENCE TO RELATED APPLICATIONS

The present application is a continuation-in-part patent application Ser. No. 08/949,472, of U.S. Pat. No. 5,955,667, issued on Sep. 21, 1999, and titled MOTION ANALYSIS SYSTEM, the entire disclosure of which is incorporated herein by reference.

Field of the Invention

The invention relates to a method and apparatus for measuring gait kinematics such as, for example, acceleration, velocity and position of gait based on foot movement analysis.

Background of the Invention

The measurement and characterization of gait (i.e. human or animal) is performed by a wide range of methods. At one end of the scale is the measurement and analysis possibilities found in a well equipped bio-mechanical lab. The equipment in these labs typically includes automated 3D optical measurement systems, force plates and physiological output indicators. The output from these transducers are fed into a central computer that enables a wide range of analysis and display possibilities. At the other end of the spectrum is the simplified analysis performed with a ruler, stopwatch and trained clinical observations.

The reasons determining gait kinematic properties (such as acceleration, velocity and position) range from: (i) personal interest, (ii) training and performance considerations of the serious athlete, (iii) rehabilitation of the disabled or (iv) for the design and analysis of footwear.

From an athletic point of view, runners, joggers and walkers often like to know how far they have journeyed and how fast they have traveled, but have had only limited cumbersome ways to measure distance and speed. Distance can be measured after the fact with a calibrated bicycle or automobile or by traveling on a known premeasured route. For determining one's speed, a simple approach is to travel a known, fixed distance on a track or road and then record the length of time required to cover the distance. This method suffers from several limitations including (i) limited walking/running routes, (ii) speed indication at measured intervals only and (iii) only an average velocity is determined over the given distance.

There are a number of portable pedometers that attempt to tackle the problem of measuring both distance and velocity. However, they have failed to gain wide spread use, because these devices are essentially limited to stride counting. Distance and speed can only be estimated if stride length consistency is assumed. This approach is inaccurate because an individual's stride length changes considerably from day to day or even within one session due to changes in terrain, fatigue, interval training, or other factors.

U.S. Pat. No. 3,355,942 discloses a pedometer that counts strides based on compression cycles in a bellows under the heel and then estimates distance based on average stride length. The invention described in U.S. Pat. No. 4,741,001 uses a spirit-biased pendulum to count strides. The pedometer disclosed in U.S. Pat. No. 4,649,552 uses a step sensor sealed into an insole to count strides. The pedometer of U.S. Pat. No. 4,651,446 counts strides by detecting flexion of the instep. Other counting pedometers include those under U.S. Pat. Nos. 5,117,444, 5,065,414, 4,855,942, 4,510,704, 4,460,823, 4,371,945, 4,322,609, 4,053,755, 3,818,194 and 3,635,399.

The majority of the patented pedometers are simply different methods of stride counting and do not address the problem of varying stride length. However, a pedometer listed under U.S. Pat. No. 4,371,945 uses ultrasonic emitters and sensors on alternate legs to measure the maximum distance between legs during each stride. While this is a significant improvement, this is only suitable for simple, low-speed gait patterns (no flight stage) and requires two sets of transducers; one on each leg.

U.S. Pat. No. 5,097,706 describes a device for taking measurements of various components of the movement of a horse. The device carries six accelerometers disposed to measure accelerations along the x, y and z axis.

Another U.S. Pat. No. 5,724,265 teaches a device that measures distance traveled, speed and height jumped of a person while running or walking. The device includes accelerometers and rotational sensors.

The broad concept of using accelerometers for determining the velocity and distance traveled, for example by athletes, is also described in German Patent 4,222,373. This patent describes the use of an accelerometer and integration to determine velocity and route or position. This device apparently processes acceleration data continuously and thus has an accumulated error from drift so that in very short period of time, the resulting data contains significant inaccuracies. The inventor indicates that this device is useful for skiers, surfers, sailors, cyclists, etc. and thus is not related to a striding device or for measuring the kinematics of striding and would not be effective for that purpose.

The Russian Patents 862074 and 885879 both by Volkov describe the attempts to overcome accumulated error in acceleration measuring devices by using a bar generator in combination with a summator and integrator. This described device does not make use of updated reference points and is thus also prone to accumulated drift.

A paper entitled "Estimation of Speed and Inclination of Walking Using Neural Networks" by Aminian et al., Published in the *IEEE, Transactions on Instrumentations and Measurements*; Volume 44 #3, June 1995, describes a portable data logger designed to record body accelerations during walking and uses three orthogonal accelerometers placed on the waistbelt to measure forward, vertical and heel acceleration. By means of neural networks, it correlates the recorded signals to the desired gait velocity and angle of incline. The generality of this method is questionable and no other gait information is produced.

BRIEF DESCRIPTION OF THE PRESENT INVENTION

The purpose of the device described herein is to provide a means to measure and display several gait parameters (that may include instantaneous and average accelerations and velocities as well as total distance traveled) by means of a simple, low-cost, portable device that can accommodate a wide variety of gaits and varying stride length. The device can be used for human or animal study.

The present invention measures various results about each individual stride rather than assuming a given fixed length. With suitable signal processing, the device can accurately determine velocity and distance traveled. The present invention can be modified to give many other useful indicators to the user such as pronation angles and impact forces. Because it is based on acceleration measurements and analysis, it inherently contains data that correlate directly to impact forces. When integrated, the acceleration data yields both instantaneous and average velocity. A second integration of these signals yields distance information such as, for example, total distance traveled, stride length and height of foot off the ground. Other relevant pieces of information include stride rate (ie. cadence) and peak foot velocity. The invention also has the potential to measure biomechanic parameters such as force of impact and gait sway and can be used for off-angle feet.

In broad terms, the present invention relates to a method of determining gait kinematics for a subject in each of a plurality of strides comprised during each stride defining a fresh datum plane, determining angles between a pair of accelerometers and said datum plane, said pair of accelerometers being adapted to measure acceleration in two directions, the two directions being separated by a known angle of greater than 0°, and being adapted to measure acceleration in a plane of motion substantially perpendicular to said datum plane, measuring acceleration in said plane of motion in said two directions, converting said accelerations to provide determination of a gait kinematic result for each said stride.

The two directions are preferably separated by an angle of between about 45° to 135° and more preferably are substantially mutually perpendicular to facilitate determination of the gait kinematic result.

The gait kinematic result can be, for example, details of foot motion, acceleration in a selected direction, velocity in a selected direction or distance in a selected direction. The selected direction is preferably either, parallel to the datum plane and in said plane of motion or perpendicular to said datum plane and in said plane of motion.

The gait kinematic result can be integrated to provide further gait kinematic results. As an example, acceleration in a selected direction can be integrated to determine velocity in a selected direction. In addition, velocity in a selected direction can be integrated to determine distance traveled in a selected direction.

The fresh datum plane is preferably defined when the pair of accelerometers are at a selected position relative to the datum plane. In particular, preferably, it can be determined that the pair of accelerometers are in the selected position by monitoring for foot impact with a surface just prior to the stance phase of the gait. The impact is defined by, for example, a rapid deceleration as determined by the pair of accelerometers or by a switch etc. actuated by impact. In one embodiment, the fresh datum plane is defined at impact plus 0.1 seconds, which is an estimate of the time, in a normal running stride, when the a sole plane of the foot is at rest on a surface in the stance phase of the gait. At this point, the angle between the accelerometers and the datum plane is reset to its original selected value. The original selected value defines the angle between one of the accelerometers and the datum plane, when the foot is at rest or in the stance phase. For example, where one of the accelerometers is positioned parallel to the datum plane during stance phase, the original selected value will be zero.

The duration of a stride (ie. when a stride begins and ends) can be determined in any suitable way. In one embodiment, the stride is determined to be the activity between when the pair of accelerometers are at a selected position relative to the datum plane. In a preferred embodiment, the beginning and end of a stride are determined by observation of impact between the foot and a surface.

Preferably, the method includes further steps for correcting for drift error.

In one embodiment, the subject's mass is determined and used to determine impact force.

In another embodiment, the method includes measuring acceleration in a lateral direction out of the plane of motion and converting said accelerations measured by the pair of accelerometers and the lateral accelerometer to provide determination of a gait kinematic result.

Broadly the present invention also relates to a device for measuring gait kinematics comprising means for mounting a pair of accelerometers in a fixed relationship to a datum plane defining surface and said pair of accelerometers being adapted to measure acceleration in two directions, the two directions being separated by a known angle of greater than 0°, means defining a datum plane for each stride for which said gait kinematics is measured as a plane occupied by said datum plane defining surface when said datum plane defining surface is in a substantially stationary position in a stance phase of said stride, means for determining angular orientation of said accelerometers to said datum plane, means for determining a gait kinematic result based on measurements of acceleration by said pair of accelerometers and said determined angular orientation of said accelerometers to said datum plane.

The two directions are preferably separated by an angle of between about 45° to 135° and more preferably are substantially mutually perpendicular to facilitate determination of the gait kinematic result.

The gait kinematic result can be, for example, details of foot motion, acceleration in a selected direction, velocity in a selected direction or distance in a selected direction. The selected direction is preferably either, parallel to the datum plane and in said plane of motion or perpendicular to said datum plane and in said plane of motion.

The device can preferably include a means for adjusting for drift error correction. A suitable means for drift error correction can include a system for determining the mean signal of any particular gait signal and applying the mean signal to the particular gait signal prior to integration to determine further gait kinematic result. In another embodiment, the means for adjusting for drift error correction is a system for using known physical limits of the derived signal such as, for example, velocity to account for drift.

Preferably said means for determining angular orientation of said accelerometers to said datum plane comprises of a pair of spaced substantially parallel accelerometers mounted in fixed relation to said datum plane defining surface and means for calculating angular orientation based on differences in accelerations measured by said pair of spaced substantially parallel accelerometers.

In one embodiment, useful for gait kinematic studies of off-angle feet, a lateral accelerometer is mounted in a fixed and known relationship to the pair of accelerometers and adapted to measure acceleration in a third direction selected to be different than the two directions and out of the plane of motion. Preferably, the lateral accelerometer is substantially perpendicular to the pair of accelerometers. The device can include a means for converting the acceleration measurements from the pair of accelerometers and the lateral accelerometer with angular orientation information to determine a gait kinematic result.

In broad terms, the present invention also relates to a method of determining gait kinematics comprised during each stride defining a datum plane, determining angles between a pair of accelerometers and said datum plane, said pair of accelerometers being adapted to measure acceleration in two directions, the two directions being separated by a known angle of greater than 0° and being adapted to measure acceleration in a plane of motion substantially perpendicular to said datum plane, measuring acceleration in said plane of motion in said two directions, converting said accelerations to provide determination of a gait kinematic result for each said stride and adjusting for drift error correction in said gait kinematic result.

The two directions are preferably separated by an angle of between about 45° to 135° and more preferably are substantially mutually perpendicular to facilitate determination of the gait kinematic result.

The gait kinematic result can be, for example, details of foot motion, acceleration in a selected direction, velocity in a selected direction or distance in a selected direction. The selected direction is preferably either, parallel to the datum plane and in said plane of motion or perpendicular to said datum plane and in said plane of motion.

The step of adjusting for drift error correction can be carried out in various ways. In one embodiment, the adjusting step is made prior to the step of converting to provide a gait kinematic result while, in another embodiment, the adjusting is conducted after the step of converting. Adjusting can be made by data modification such as in the determination of the accelerations or the gait kinematic result or by modification of the determined gait kinematic result, such as by employing known limitations in the derived signal to adjust for the drift error correction. The adjusting step can provide correction which reduces or removes the drift error.

In one embodiment, the method further comprises one or more integration steps to derive further gait kinematic results from the gait kinematic result. Adjusting for drift error correction can be conducted in any or all of the these integration steps. As an example, in one embodiment, the gait kinematic result is acceleration in a selected direction and the method further comprises integrating said acceleration in said selected direction to determine velocity in said selected direction. In such an embodiment, adjusting for drift error correction can be made by determining a mean acceleration in said selected direction and removing the mean acceleration from the acceleration in said selected direction prior to integrating to determine velocity in said selected direction. This adjusting step can be done in each stride. Mean values from one stride can be used for drift error correction in a subsequent stride.

The method can further comprise integrating said velocity in a selected direction to determine distance traveled in a selected direction and, if desired, drift error correction can be made by determining a mean velocity in said selected direction and removing the mean velocity from the velocity in said selected direction prior to integrating to determine distance traveled in a selected direction.

The datum plane is preferably defined when the pair of accelerometers are at a selected position relative to the datum plane. In particular, preferably, it can be determined that the pair of accelerometers are in the selected position by monitoring for foot impact with a surface just prior to the stance phase of the gait. The impact is defined by, for example, a rapid deceleration as determined by the pair of accelerometers or by a switch etc. actuated by impact. In one embodiment, the fresh datum plane is defined at impact plus 0.1 seconds, which is an estimate of the time, in a normal running stride, when the a sole plane of the foot is at rest on a surface in the stance phase of the gait. At this point, the angle between the accelerometers and the datum plane is reset to its original selected value. The original selected value defines the angle between one of the accelerometers and the datum plane, when the foot is at rest or in the stance phase. For example, where one of the accelerometers is positioned parallel to the datum plane during stance phase, the original selected value will be zero. The datum plane resetting can alternatively use gait speed or foot plant duration information to modify the fresh datum plane selection.

In another embodiment, the method further comprises converting said accelerations to provide acceleration substantially parallel to the datum plane and integrating said acceleration substantially parallel to the datum plane to define stride velocity and, if desired, drift error correction can be made by determining a mean horizontal acceleration and removing the mean acceleration substantially parallel to the datum plane from the acceleration substantially parallel to the datum plane prior to integrating to determine stride velocity.

In one embodiment, the method further comprises integrating said velocity in a selected direction to define distance in said selected direction. Drift error correction can be made by determining a mean velocity in a selected direction and removing the mean velocity in a selected direction from the velocity in a selected direction prior to integrating to determine distance in a selected direction.

Preferably said velocity in a selected direction is averaged over a plurality of strides to provide average velocity.

In another embodiment, the step of adjusting for drift error correction employs known limitations in the derived signal. As an example, in a preferred embodiment the gait kinematics for velocity substantially parallel to the datum plane are determined and the velocity is adjusted such that no velocity value is negative, as velocity values are limited to a value greater than or equal to zero.

Preferably said datum plane is defined by the position of a sole plane when said sole plane is at rest on a surface in a stance phase of said gait and wherein said pair of accelerometers are positioned in fixed relationship to said sole plane.

Preferably said step of determining angles of a pair accelerometers is based on measurements of a pair of spaced substantially parallel accelerometers positioned at a selected angle to said sole plane.

In one embodiment, the method determines the gait kinematics in each of a plurality of strides and a fresh datum plane is defined for each stride.

Broadly the present invention also relates to a device for measuring gait kinematics comprising means for mounting pair(s) of accelerometers in a fixed relationship to a datum plane defining surface and said pair of accelerometers being adapted to measure acceleration in two directions, the two directions being separated by a known angle of greater than 0°, means defining a datum plane measured as a plane occupied by said datum plane defining surface when said datum plane defining surface is in a substantially stationary position in a stance phase of said stride, means for determining angular orientation of said accelerometers to said datum plane, means for determining a gait kinematic result based on measurements of acceleration by said pair of accelerometers and said determined angular orientation of said accelerometers to said datum plane and means for adjusting for drift error correction.

The two directions are preferably separated by an angle of between about 45° to 135° and more preferably are substantially mutually perpendicular to facilitate determination of the gait kinematic result.

The gait kinematic result can be, for example, details of foot motion, acceleration in a selected direction, velocity in a selected direction or distance in a selected direction. The selected direction is preferably either, parallel to the datum plane and in said plane of motion or perpendicular to said datum plane and in said plane of motion.

The means for adjusting for drift error correction can include a system for determining the mean signal of any particular gait signal and applying the mean signal to a selected signal prior to integration to determine further gait kinematics. In another embodiment, the means for adjusting for drift error correction is a system for using known physical limits of the derived signal such as, for example, velocity to account for drift.

Preferably said means for determining angular orientation of said accelerometers to said datum plane comprises of a pair of spaced substantially parallel accelerometers mounted in fixed relation to said datum plane defining surface and means for calculating angular orientation based on differences in accelerations measured by said pair of spaced substantially parallel accelerometers.

Preferably said device further comprises means for converting the accelerations in two directions to obtain acceleration in said selected direction.

Preferably said device further comprises means for converting the acceleration in said selected direction to velocity in said selected direction or to distance in said selected direction by means of integration.

In accordance with another broad aspect fo the present invention, there is provided a device for measuring gait kinematics of a stride in a subject having an foot comprising means for mounting a pair of accelerometers in a fixed relationship to a datum plane defining surface and said pair of accelerometers being adapted to measure acceleration in two substantially parallel directions about an axis of rotation defined by movement of the foot, means defining a datum plane measured as a plane occupied by said datum plane defining surface when said datum plane defining surface is in a stationary position in a stance phase of said stride, and means for calculating angular orientation based on differences in accelerations measured by said pair of accelerometers.

Preferably the axis of rotation is substantially parallel to the subject's sagittal plane and to the datum plane defining surface and, in a particularly preferred embodiment, is that axis about which the foot pronates.

In accordance with another broad aspect, a method of determining pronation characteristics of a foot during a stride is provided comprising during each stride defining a datum plane, determining angular acceleration about an axis about which a foot pronates, converting the angular acceleration relative to the datum plane to determine an angle of pronation for the foot.

BRIEF DESCRIPTION OF THE DRAWINGS

Further features, objects and advantages will be evident from the following detailed description of the preferred embodiments of the present invention taken in conjunction with the accompanying drawings in which;

FIG. 3A is a view similar to FIG. 6 but showing a preferred arrangement.

FIGS. 4Aa, 4Ab and 4Ac are plots of upper tangential acceleration, lower tangential acceleration and normal acceleration respectively versus time.

FIG. 5A is a plot of foot acceleration during a single step.

DESCRIPTION OF THE PREFERRED EMBODIMENTS

Figure 1:
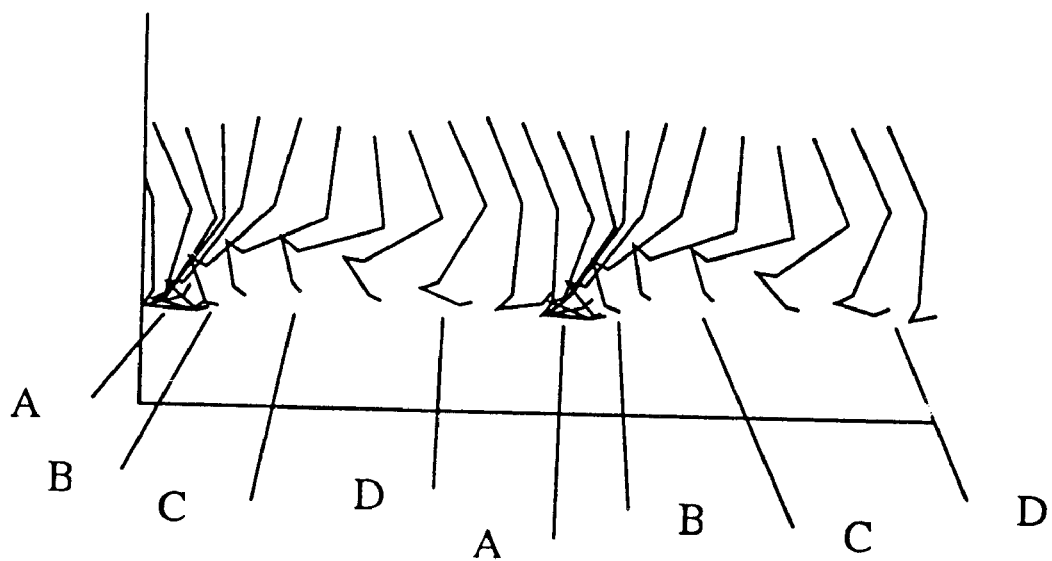
FIG. 1 is a schematic illustration of leg movement during walking or running.

FIG. 1 shows various stages of gait in a runner (two complete gait cycles are shown). The foot plants on the ground or supporting surface and comes to a complete rest in what is known as the stance phase of gait cycle as indicated at Points A in FIG. 1. The foot then begins to accelerate as indicated at B in FIG. 1 as the toe prepares to take off. The swing phase indicated at C follows as the leg passes through the air. Following this, the foot decelerates as it prepares to strike the ground as indicated at D and then repeats the cycle. These accelerations, decelerations and stoppings are utilized in the present invention to determine gait kinematics as will be described below.

The fact that the foot plants and it becomes at rest or stationary during the stance phase A is used to provide a datum position to define a datum plane for each stride of the gait thereby eliminating accumulated error that would be adherent in the process if it wasn't iterated commencing at each stance phase A.

Figure 6:
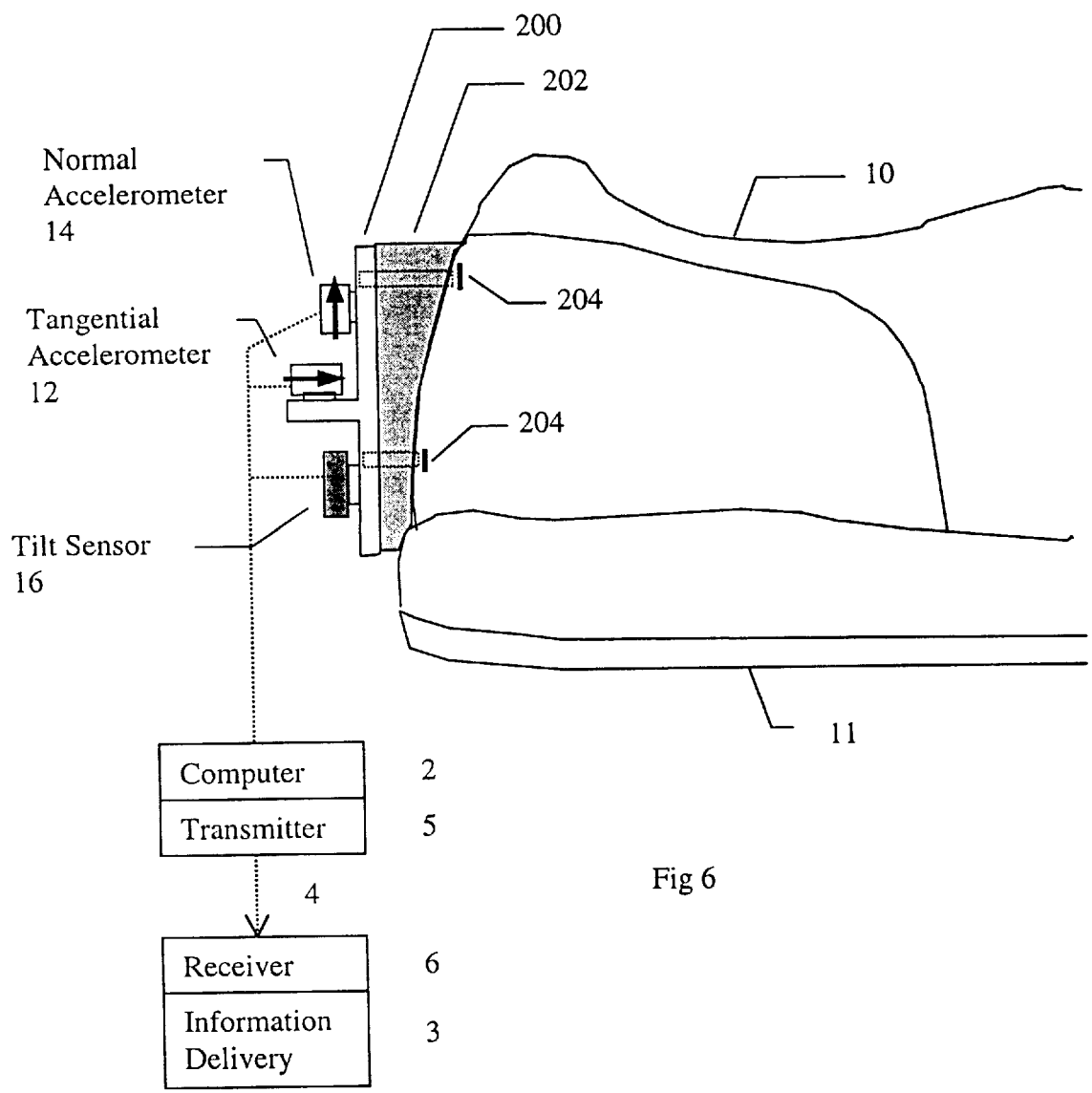
FIG. 6 is a more detailed illustration of the accelerometers mounted on the shoe, and schematically illustrating their connection to a computer.

The information to permit gait kinematic investigations is obtained via suitable sensors preferably acceleration sensors (accelerometers) 12 and 14 and a tilt sensor 16 and this information is fed to a suitable computer 2 that performs calculations transferred from the data from the accelerometers into the information format for delivery system 3 and displayed in the selected format (see FIG. 6).

The information may be transferred directly as represented by the arrow 4 or transferred by a transmitter 5 and then picked up by a receiver 6 in the display unit.

Figure 2:
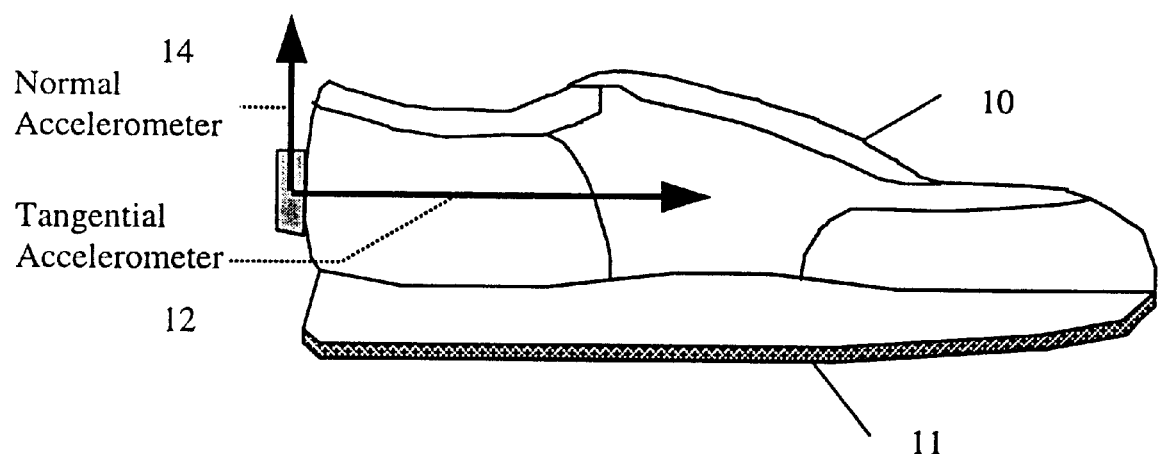
FIG. 2 shows a shoe with accelerometers mounted thereon.

Two accelerometers 12 and 14 are mounted on the heel counter of shoe 10. While the accelerometers can be disposed at any known and fixed position relative to each other to measure acceleration in two directions. Preferably, accelerometers 12 and 14 are mutually substantially perpendicular to facilitate data generation. A tilt sensor 16 (see FIG. 6) is also mounted on the heel counter of shoe 10. Accelerometers 12 and 14 and tilt sensor 16 are in fixed position relative to a datum plane defining surface, which in the illustrated embodiment is a plane 11 defined by the sole of the shoe 10 as will be described below. The accelerometers are preferably (but not necessarily) orthogonally mounted as shown such that in the neutral standing position one is oriented vertically and one horizontally (FIG. 2). The vertical accelerometer 14 is referred to as the normal accelerometer and the horizontal accelerometer 12 is referred to as the tangential accelerometer. These accelerometers measure the accelerations of the foot as the leg traverses through a plane parallel to the sagittal plane. While it is preferred to align these with one accelerometer (e.g. accelerometer 12) substantially parallel to the sole plane 11 and the other 14 substantially perpendicular thereto this is not essential.

The tilt angle θ is the angle between a datum plane 100 which (FIG. 3a), as will be described below is defined by a surface represented by the sole plane 11 of the foot or shoe 10. The sole plane 11 has a fixed orientation relative to the two accelerometers 12 and 14, (i.e. the sole of the shoe 10 defines a plane and the position of the sole on the shoe 10 in the stance position of the gait defines the datum plane 100 for the next stride). The angle θ is the instantaneous angle between the plane 11 defined by the sole and the previously defined datum plane 100 for that particular stride (see FIG. 3a).

Figure 3A:
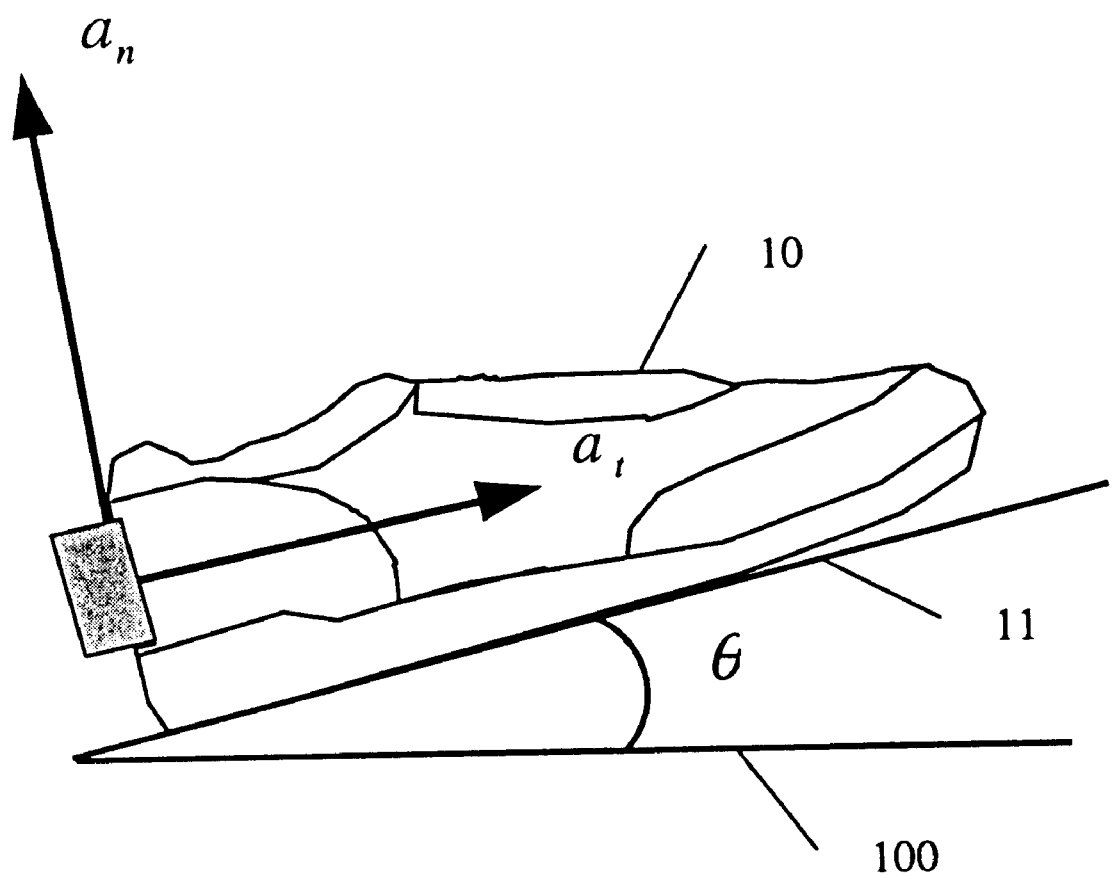
FIGS. 3a and 3b the various angles and movement vectors of the shoe.

As the shoe 10 is tilted during the stride, the accelerometers 12 and 14 measure the accelerations $a_t$ and $a_n$ in their respective directions as depicted in FIG. 3a. Knowing the foot angle θ at any point in time, these accelerations may be resolved into their components in the selected direction, but normally are resolved to a direction substantially parallel to the direction of the plane 100 (referred to below as the horizontal direction as it will generally be approximately horizontal) and then added together (with vectors) yielding the net acceleration in the horizontal direction (see FIG. 3b).

Since the accelerometers are mounted in the plane of motion 102 (see FIG. 3b) the net acceleration is also parallel to the plane of motion 102, i.e. the direction in which the stride is taken. This gait kinematic result for horizontal acceleration can be calculated by the following equation:

$$a_x = a_t \cos(\theta) - a_n \sin(\theta)$$

where $a_x$=acceleration in horizontal direction
$a_t$=acceleration of tangential accelerometer 12
$a_n$=acceleration of normal accelerometer 14
θ=angle of tilt of accelerometer 12 (i.e. sole 11 of shoe 10 with respect to plane 100 which in normal operation will represent the ground or surface on which the stride is taking place.)

Figure 4A:
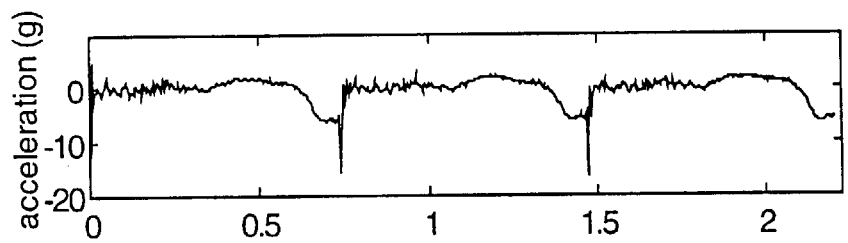
FIGS. 4a, 4b and 4c are graphs of tangential acceleration, normal acceleration and angle of tilt of the foot respectively versus time.
Figure 4B:
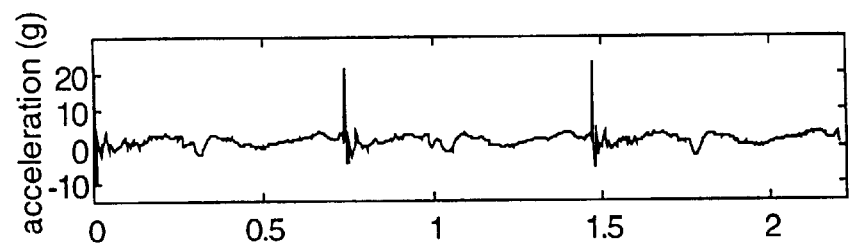
Figure 4C:
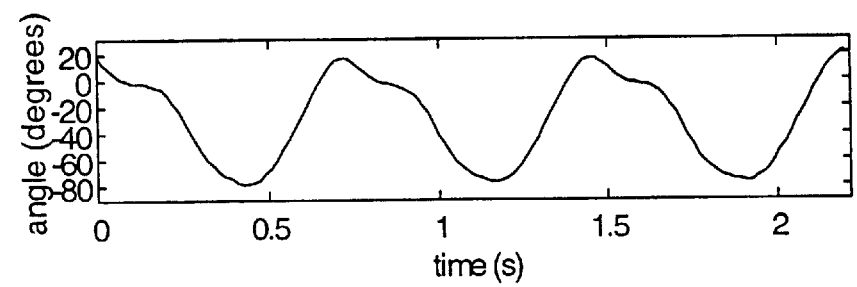

FIGS. 4a, b, c show typical data gathered over several gait cycles for the two mutually perpendicular accelerometers 12 and 14 and tilt sensor 16 versus time in second(s). This includes data collected by the tangential accelerometer (FIG. 4a), by the normal accelerometer 14 (FIG. 4b) and finally, FIG. 4c shows the angle of foot tilt through the gait cycles.

Figure 5A:
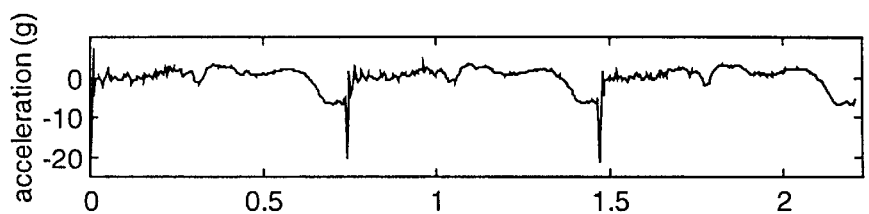
FIGS. 5a, 5b and 5c are plots of horizontal acceleration, foot velocity and speed of travel respectively versus time.
Figure 5B:
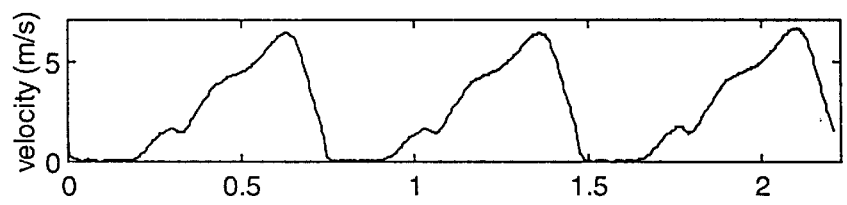
Figure 5C:
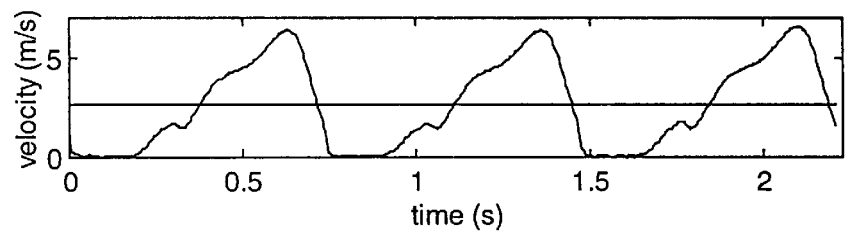

The net horizontal acceleration $a_x$, shown in FIG. 5a, is integrated to yield the foot velocity as a function of time (FIG. 5b). This velocity is averaged over several studies (three studies or cycles in this example) to yield the mean speed of travel shown as a straight line in FIG. 5c. The mean velocity of the walker/runner, over the given time interval, corresponds with the calculated mean horizontal foot velocity during the same time period.

Other gait kinematic results may also be easily derived from the measured data. These include, but are not limited to, stride rate, stride length, total distance traveled as well as angular velocities and accelerations.

Primary Components

As above described, the gait speedometer shown in FIG. 6 includes two linear accelerometers and an inclinometer or tilt sensor 16 all amounted on the ankle or shoe 10 in fixed relation to the datum plane defining surface or sole 11. The required characteristics of the accelerometers and inclinometer/tilt sensor will be described and specific prototype selections that have been tested or considered are listed below.

Accelerometers:

The accelerometer transducers are mounted on the foot or shoe. It is necessary that they must not interfere or influence natural gait; this requires that they are small and lightweight.

The device may be battery powered; this requires that the primary components and associated circuits possess low-power consumption characteristics.

Human and many animal gaits are a very low frequency phenomenon; the accelerometers used in this device must be able to measure down to these frequencies.

The accelerometer cluster is mounted on the foot or shoe and will thus be subjected to large impact forces and abuse. It is necessary that the accelerometers be rugged and durable to be able to survive in this environment.

The linearity, repeatability and noise levels must be such that the accuracy of measurement is acceptable for the application.

The accelerometers used in the development work of this invention are manufactured by Analog Devices (part no.'s ADXL50 and ADXL150/250). These accelerometers make use of micro-machining techniques to build the transducer into a silicon chip. This accounts for the small size, lower power consumption and accuracy of the devices.

The invention described herein is not limited to the above mentioned accelerometer family. Other accelerometers are currently produced or are under development by different manufacturers and could be considered for this purpose. As well, other accelerometer technologies are candidates for this invention including strain-gauge and piezo-electric types.

Inclinometers/Tilt Sensors:

The transducer is mounted on the foot or shoe. It is necessary that it must not interfere or influence natural gait; this requires that it be small and lightweight.

The device may be battery powered; this requires that the primary components and associated circuits possess low-power consumption characteristics.

The transducer cluster is mounted on the foot or shoe and will thus be subjected to large impact forces and abuse. It is necessary that the inclinometers or tilt sensors be rugged and durable to be able to survive in this environment.

The linearity, repeatability and noise levels must be such that the accuracy of measurement is acceptable for the application.

To be able to determine the foot angle, many approaches are possible. It is possible to measure the foot angle directly by means of a tilt sensor or other suitable device. It is possible to measure the foot's angular velocity by means of a rate gyro or other suitable device and then integrate the signal once to determine the foot angle. It is possible to measure the foot's angular acceleration by means of an angular rotation accelerometer or other suitable device and then integrate the signal twice to determine the foot angle.

Signal processing a pair of spaced parallel accelerometers to extract tilt information from the foot's angular acceleration, will be described in more detail herein below as it is the preferred system for determining the angle θ.

Figure 7:
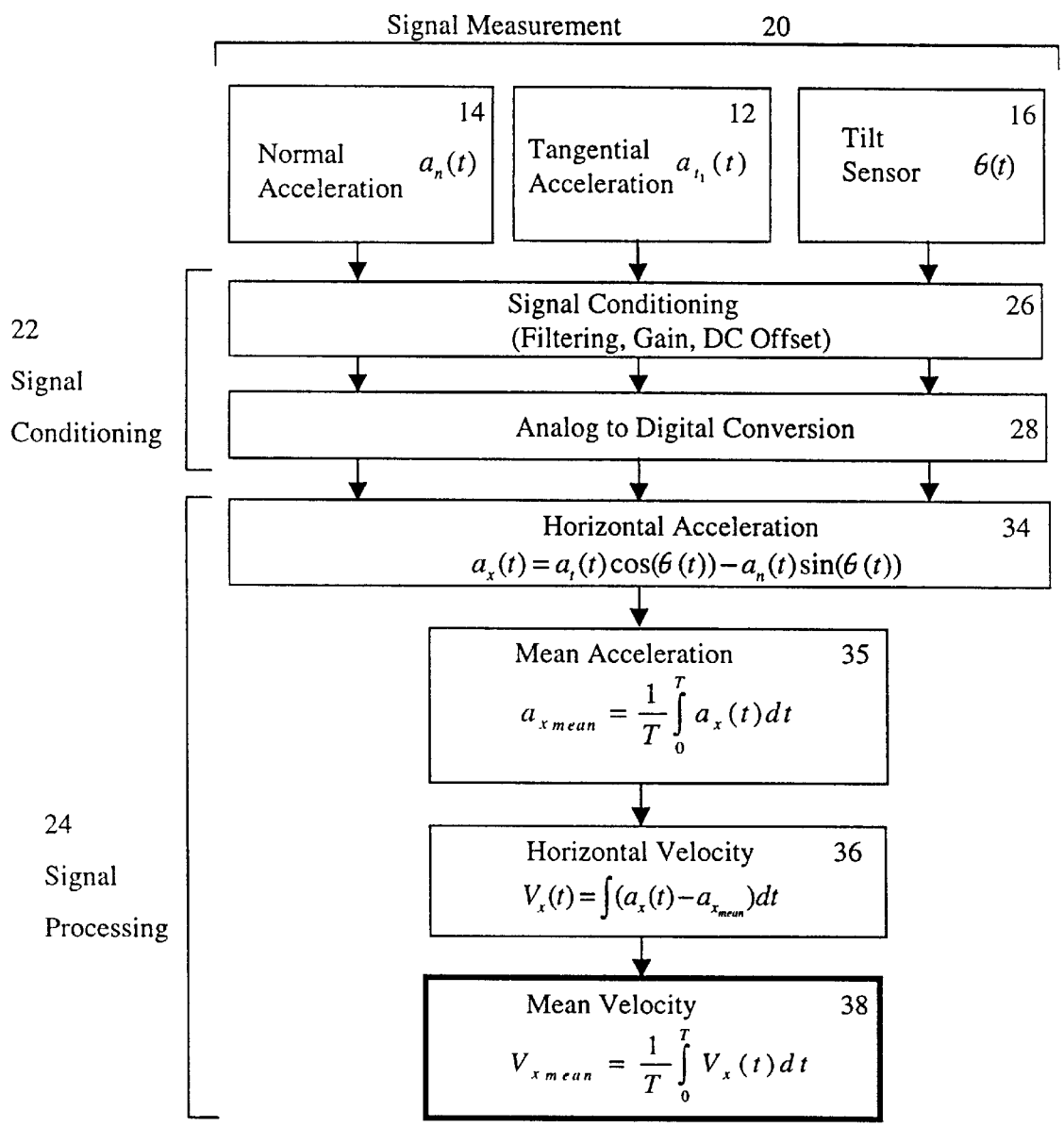
FIG. 7 is a flow diagram of one mode of operation of the computer.

Signal Conditioning:

Full implementation of the gait speedometer includes signal measurement 20, signal conditioning 22 which includes processing components such as amplifiers, filters and signal processing 24. A signal path or flow diagram shown in FIG. 7 outlines the process. Signals emerge from the three primary transducers (normal and tangential accelerometers and inclinometer) and pass through signal conditions 22 which includes signal conditioning 26, by applying zero adjustments, gains, filters, etc. and analog to digital conversion 28. These signals from the accelerometers 12 and 14 are then combined using the angle θ to determine a gait kinematic result such as, for example, acceleration in a selected direction, velocity in a selected direction or distance in a selected direction. The simplest calculation is that for acceleration in a selected direction such as net horizontal acceleration 34. From acceleration in a selected direction instantaneous foot velocity i.e. horizontal velocity 36 and mean velocity 38 may be determined.

Gait Parameter Calculation and Display:

Once the instantaneous foot velocity has been determined 36, it may if desired be transmitted via a wireless transmitter/receiver pair 5, 6 or signal wires 4 to a calculation/display unit 3 (such as a wristwatch sized device, portable calculation device or desktop computer) to store and display various velocity parameters along with many other gait indications (see FIG. 6).

More Preferred Embodiment

A second embodiment of the invention is shown and will be described with reference to FIGS. 1A to 16A inclusive. Like reference numerals are used to indicate like parts in all embodiments.

Figure 1A:
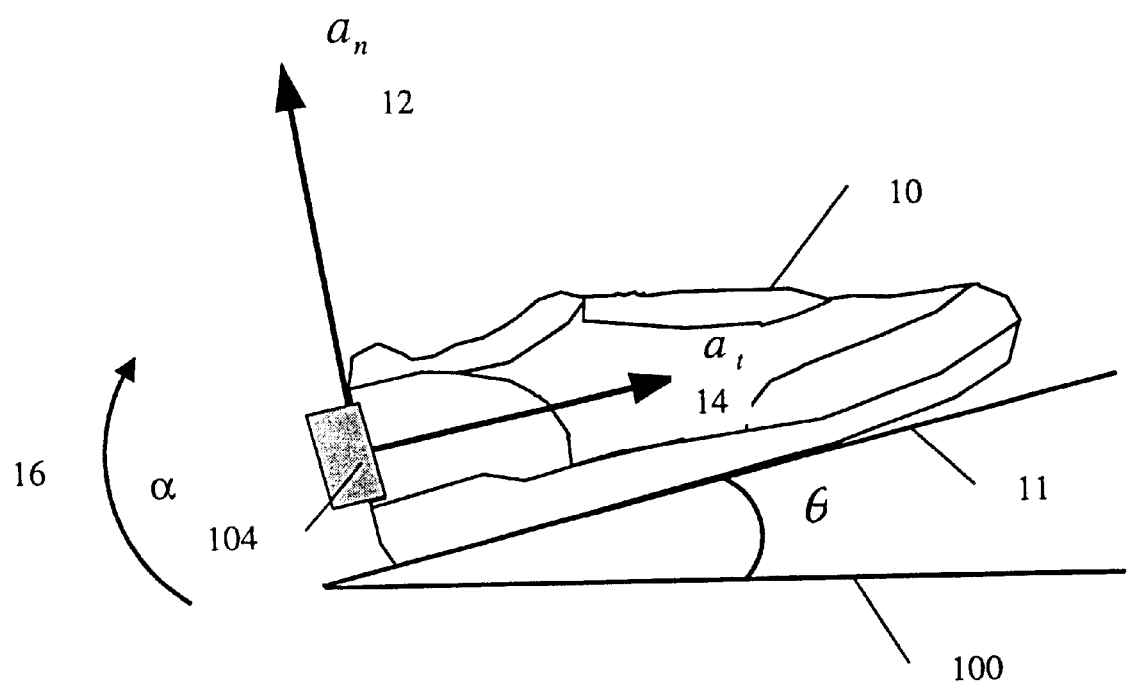
FIG. 1A shows the relationship of the normal, tangential and angular acceleration vectors and the shoe angle.
Figure 2A:
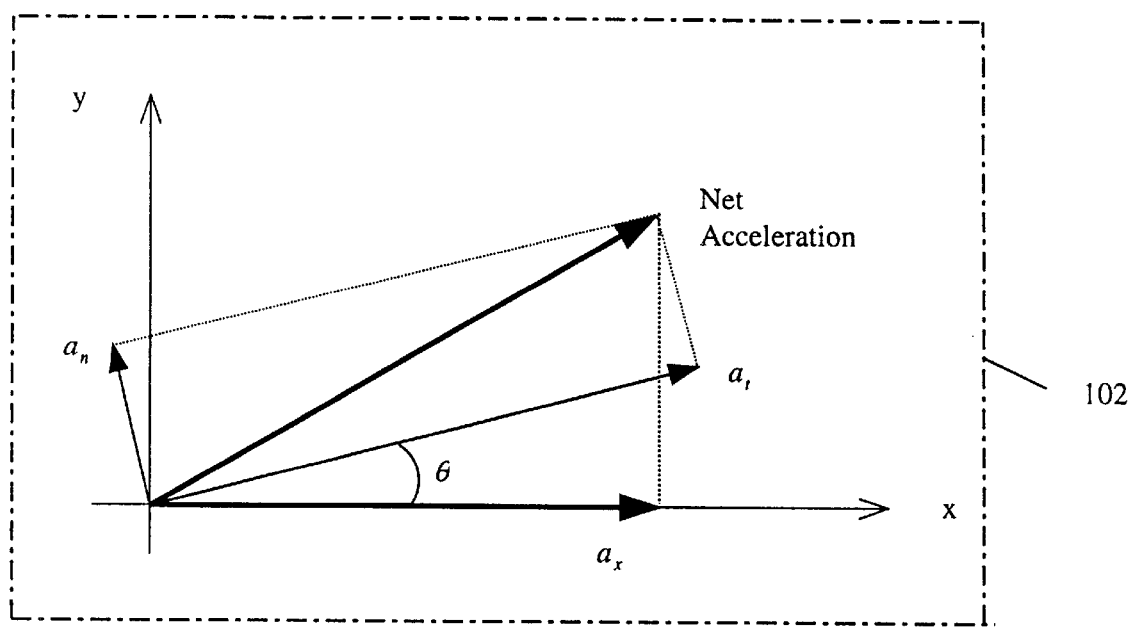
FIG. 2A shows how the vectors combine to produce the net acceleration vector.
Figure 3A:
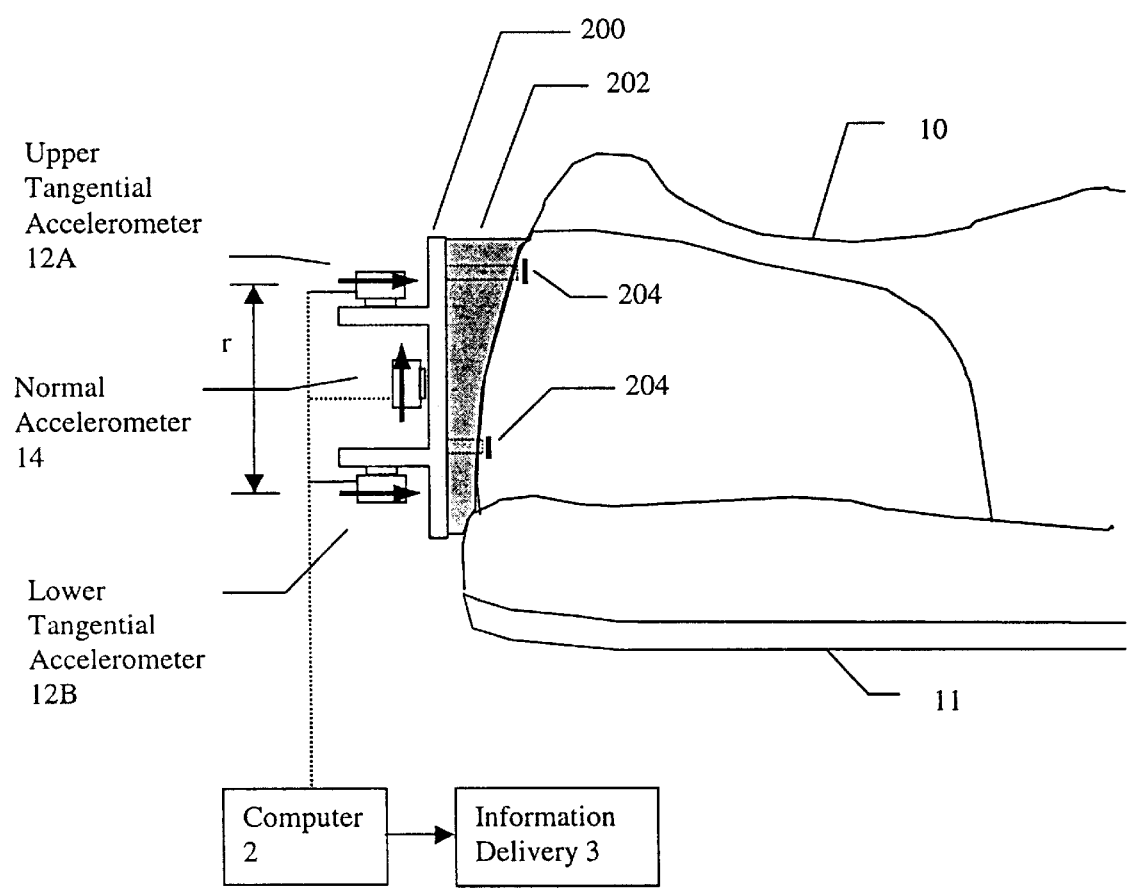
Figure 4A:
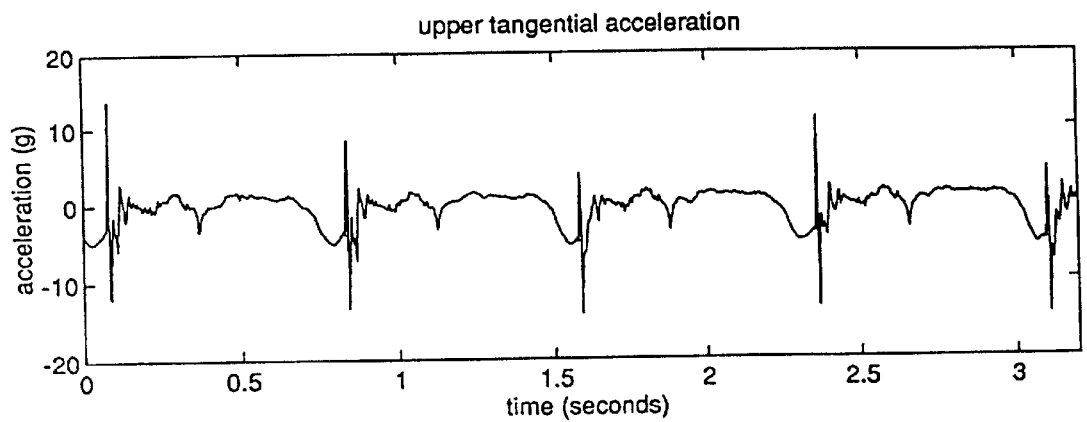
Figure 4A:
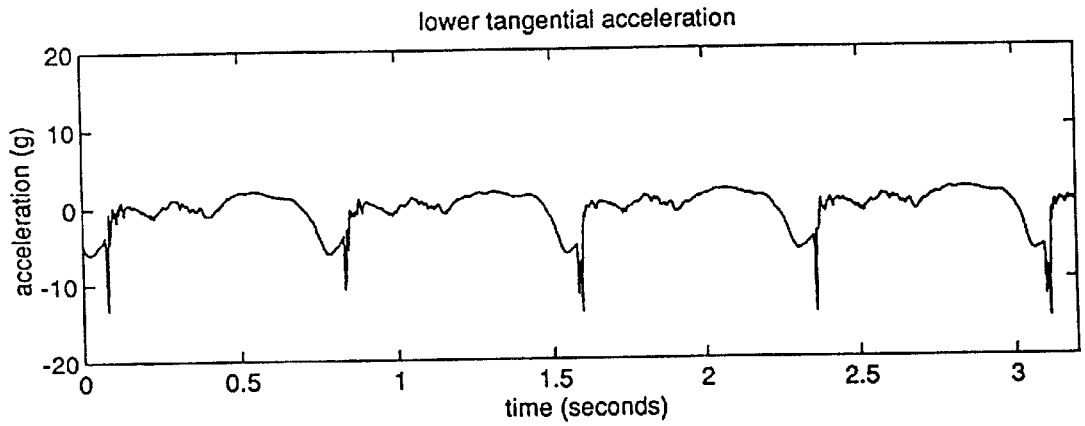
Figure 4A:
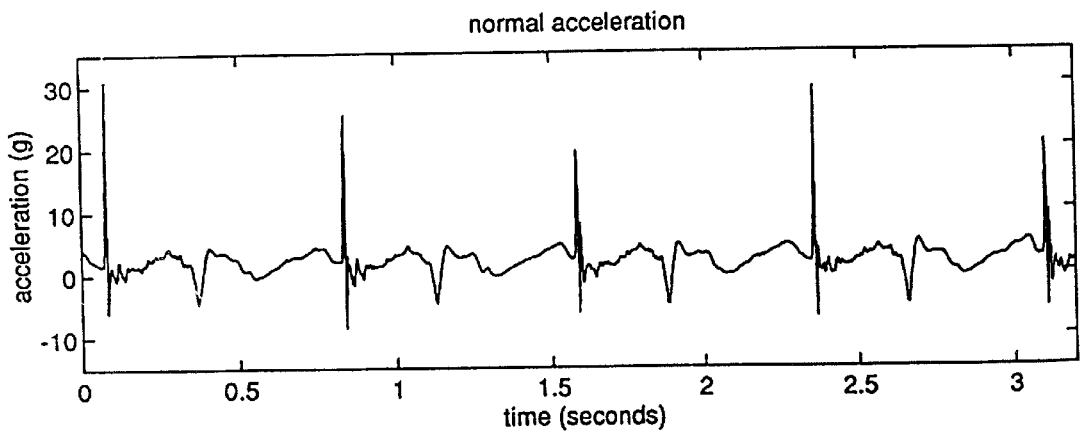
Figure 5A:
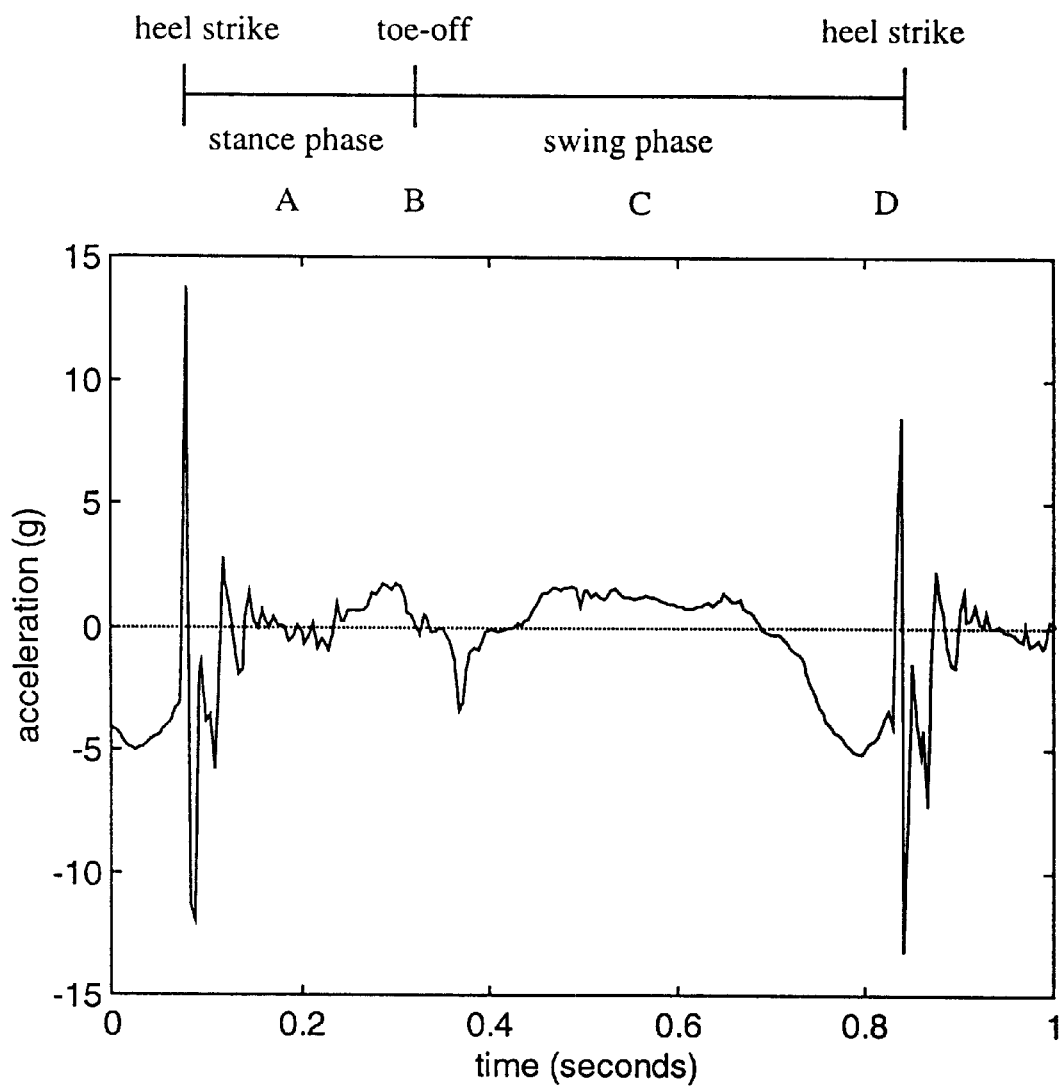

Accelerometers are placed on the foot in essentially the same manner as described above so that the normal accelerations, $a_n$, tangential accelerations, $a_t$, and angular accelerations, $\alpha$, preferably about the intersection 104 of the tangential and normal acceleration vectors $a_t$ and $a_n$ respectively can be simultaneously measured (see FIG. 1A). The normal accelerometer measures 14 acceleration perpendicular to the base or sole 11 of the foot or shoe 10 which as above described provides the datum plane 100 defining surface 11 that defines the datum plane 100 for each stride when the sole 11 is at rest in the stance phase A of each stride. The tangential accelerometer 12 is sensitive to accelerations parallel to the base or sole 11 of the foot or shoe 10. The absolute direction of these accelerations vary continuously as the foot moves through a gait cycle. The measured angular acceleration is integrated twice to yield the foot angle θ. This angle θ is then used to resolve the normal and tangential accelerations into a net horizontal acceleration as shown in FIG. 2A. The horizontal acceleration is then integrated to find the velocity of the foot as a function of time. The subject's mean speed of travel is determined by averaging the foot velocity over an integer number of foot strides.

The term horizontal or net horizontal acceleration velocity etc. is used for convenience as though the vector is horizontal i.e. parallel with a horizontal datum plane 100. This vector will normally be parallel to the datum plane 100 and the plane of motion 104. It also will be apparent that these vectors may be resolved into any selected plane or direction i.e. horizontal, vertical or somewhere in between.

It was chosen to place accelerometers on the foot because the foot follows a regular pattern of acceleration and deceleration as the foot travels through the air and comes to rest on the ground for each stride as indicated by the segments A, B, C and D of the stride in FIG. 1. The small stationary period of time when the foot rests on the ground provides a useful point of reference for each stride and is used to define the datum plane 100 for each stride. With this method, each stride is independently measured and thus there is no accumulating error if the measurement were interconnected. It makes no assumptions regarding stride length, gait type (walking, jogging or running) and it accounts for the flight phase of a running gait.

Three accelerometers (two tangential 12A and 12B and a normal 14) are mounted on a small aluminum bracket 200 fastened via a leveling wing 202 by two screws 204 to the heel counter of a shoe 10 as shown in FIG. 3A. The upper and lower accelerometers 12A and 12B provide a pair of spaced substantially parallel accelerometers that measure tangential accelerations, while the middle normal accelerometer 14 measures the normal acceleration. The angular acceleration is determined by taking the difference of the accelerations generated by the upper and lower accelerometers divided by the distance between them (shown in FIG. 3A by the distance r). It is preferred that these accelerometers 12A and 12B be equally spaced from accelerometer 14, but this is not essential. The net tangential acceleration of the foot preferably is taken as the average of the upper and lower tangential accelerometers. This data is delivered to a computer 2 that then determines the acceleration, velocity and other information which may be delivered to the use, for example, by audio or visual means such as an earphone or digital or analogue visual display or any other suitable means schematically indicated at 3.

Figure 15A:
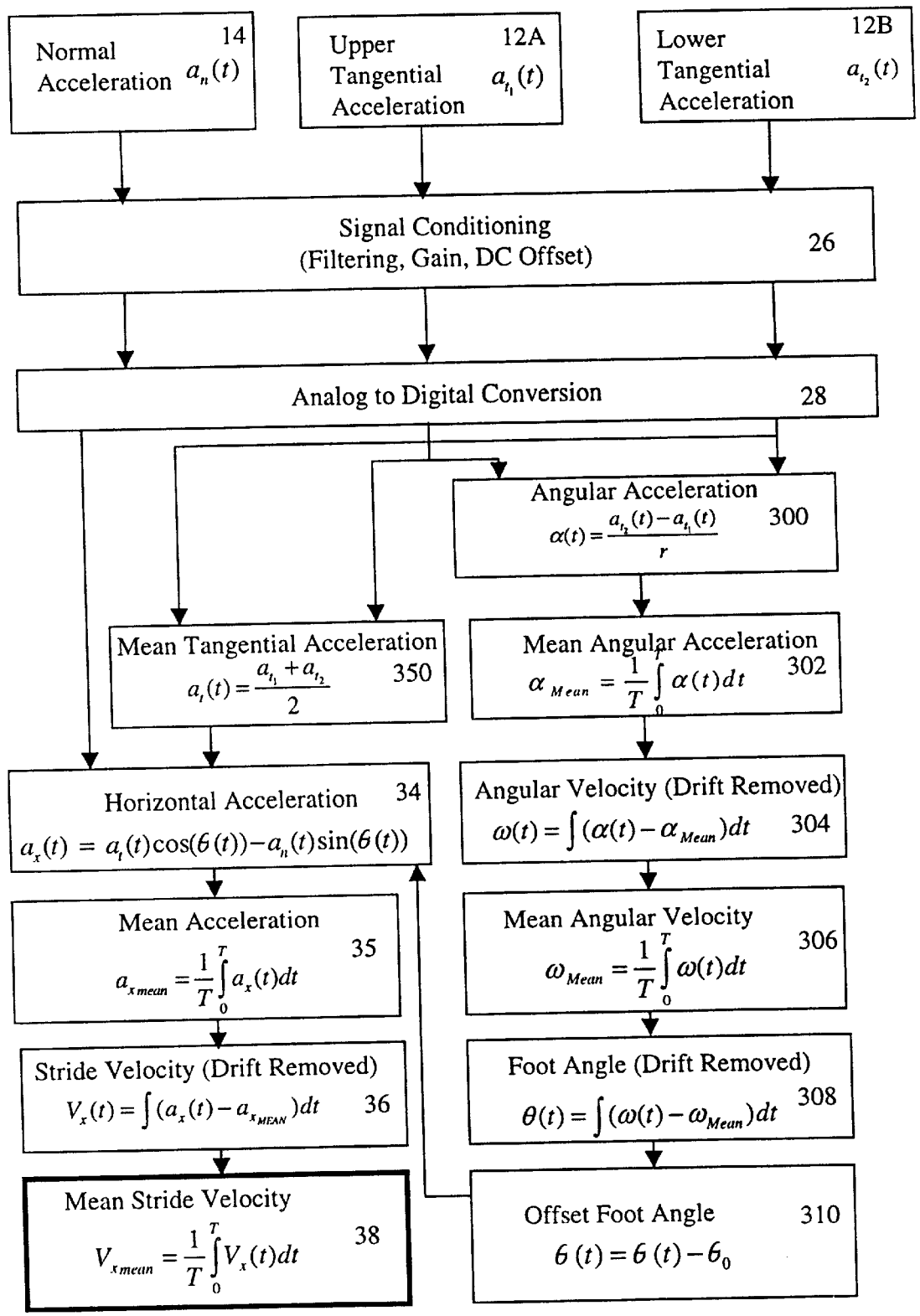
FIG. 15A is a flow diagram similar to that shown in FIG. 7.

Suitable accelerometers are those made by Analog Devices (type ADXL50AH). An analog signal generated by such an accelerometer can be converted to a digital signal in a converter 28 (FIG. 15A).

Signal Processing and Analysis

Typical normal and tangential accelerations for strides (4 in this example) of a subject jogging at 3 m/s (7 mph) are shown in FIG. 4A. A close-up of a tangential signal from the first stride shown in FIG. 4A is shown in FIG. 5A. The initial sharp spike corresponds to foot impact. The flatter section of the signal in the segment immediately following impact, is the stance phase of the gait. The negative dip in the acceleration just after toe-off corresponds to the heel being raised as the knee flexes. The positive acceleration during the middle portion of the swing phase corresponds to the foot accelerating forward. During the latter portion of the swing phase, as the foot is slowed down in preparation for contact with the ground, there is a period of negative acceleration.

Stride beginning and ending locations were found from the impact spikes when the subject's foot struck the ground. An algorithm based on finding a local maximum after the acceleration crosses a variable threshold value was used to find the impact spikes. The foot decelerates to a low speed before striking the ground but does not actually reach zero velocity until just slightly after impact. A location of approximately 0.1 seconds after foot strike was chosen to denote the beginning of a stride since this is approximately where the foot velocity is zero. This position is used to determine the datum plane 100 which corresponds with the plane of the sole 11 at this point in time. The time of 0.1 seconds works well for a normal human run. However, adjustments may be required where the gait is a walk or sprint.

Foot Angle

It is preferred to measure angular acceleration and then integrate twice to determine the foot angle θ. The measurement of the angular acceleration is accomplished by taking the difference between two parallel tangential accelerometers 12A and 12B.

After dividing the sequence into strides, the foot's angular position is determined. Coordinates are chosen so that the tilt is considered zero when the foot is in the zero velocity position i.e. the stance phase of the gait selected at 0.1 seconds after the foot strike i.e. a 0.1 second offset, and positive when the toe was pointed upwards as shown in FIG. 1A. The foot's angular acceleration is found by subtracting the upper tangential acceleration, $a_{t_1}$, from the lower tangential acceleration, $a_{t_2}$. The angular acceleration is radians/sec$^2$, α, is calculated by dividing by the distance between the two accelerometers as indicated at 300 in FIG. 15A.

$$\alpha = \frac{(a_{t_2} - a_{t_1})}{r}$$

Figure 6A:
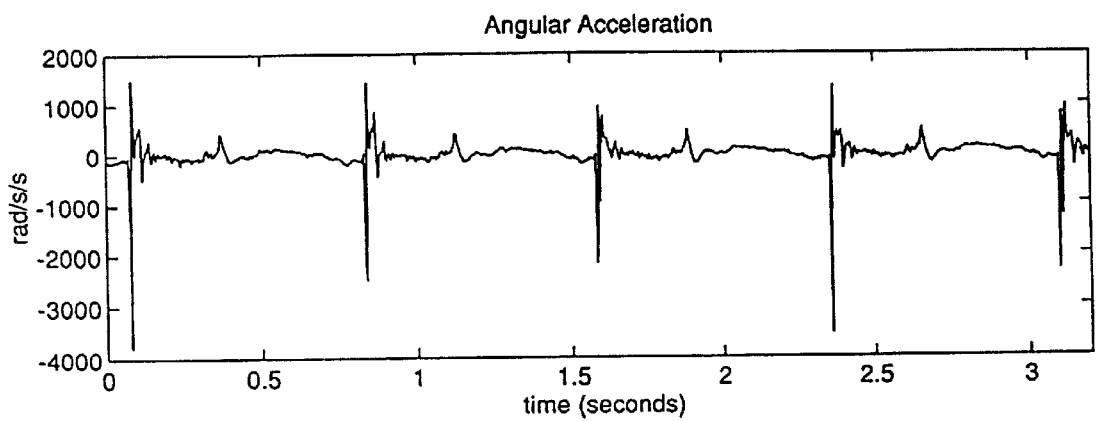
FIGS. 6Aa, 6Ab and 6Ac are plots of angular acceleration, angular velocity and angular position respectively versus time.
Figure 6A:
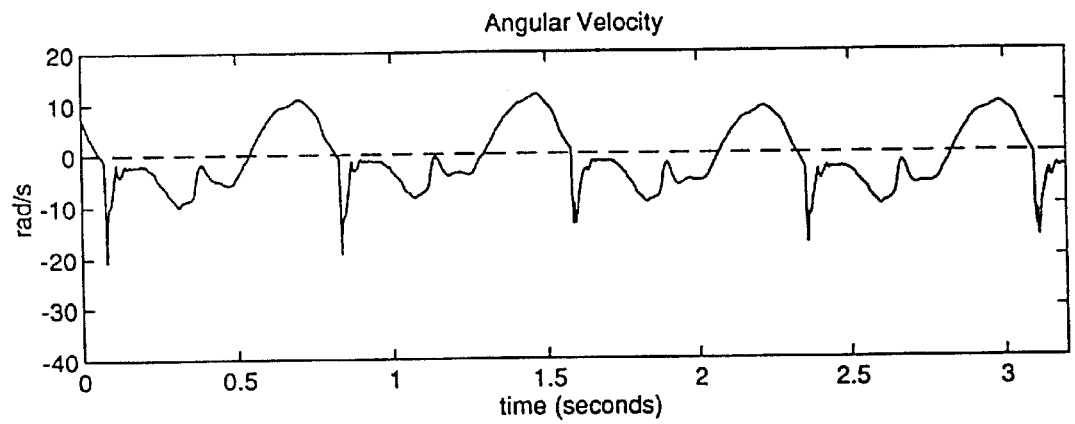
Figure 6A:
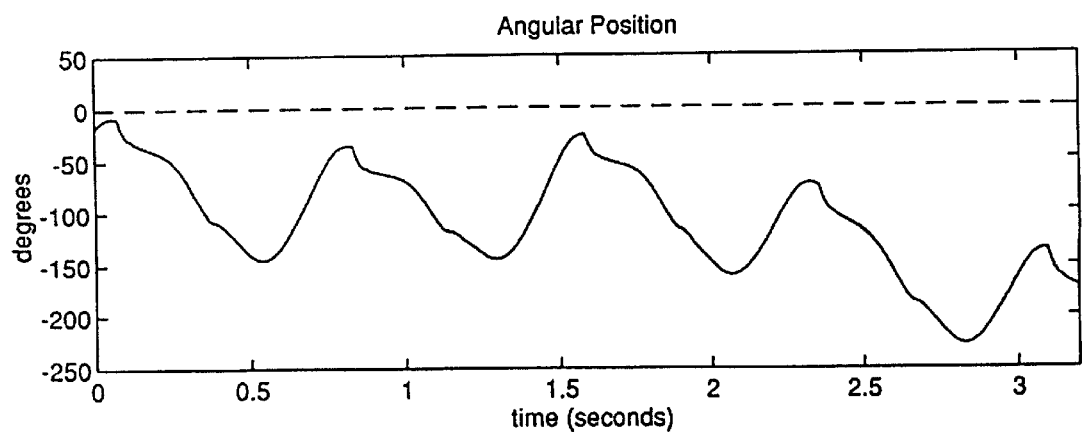

The resulting angular acceleration, from the data shown in FIG. 4A, is shown in FIG. 6A$a$. This data was then integrated using an accumulating sum and the resulting angular velocity, ω (in radians/sec) as shown in FIG. 6A$b$. This result was once again integrated to produce the foot angle, θ, shown in FIG. 6A$c$. Note how the very noisy and non-descript appearing signal in FIG. 6A$a$ is transformed into a very regular, smoothed function in FIG. 6A$c$. Low frequency drift is evident in the foot angle signal.

A preferred method to convert drift is to first determine the mean angular acceleration $\alpha_{mean}$ as indicated at 302 and to remove zero offset drift from α and ω by subtracting each signal's mean for each individual stride before integrating as indicated at 304 in FIG. 15A to define angular velocity ω.

The mean angular velocity $\omega_{mean}$ is determined as indicated at 306 in FIG. 15A and then used to compute the angle θ as indicated at 308 and the position of the datum plane 100 using the offset θ$_0$(0.1 seconds) described above as indicated at 310.

Figure 7A:
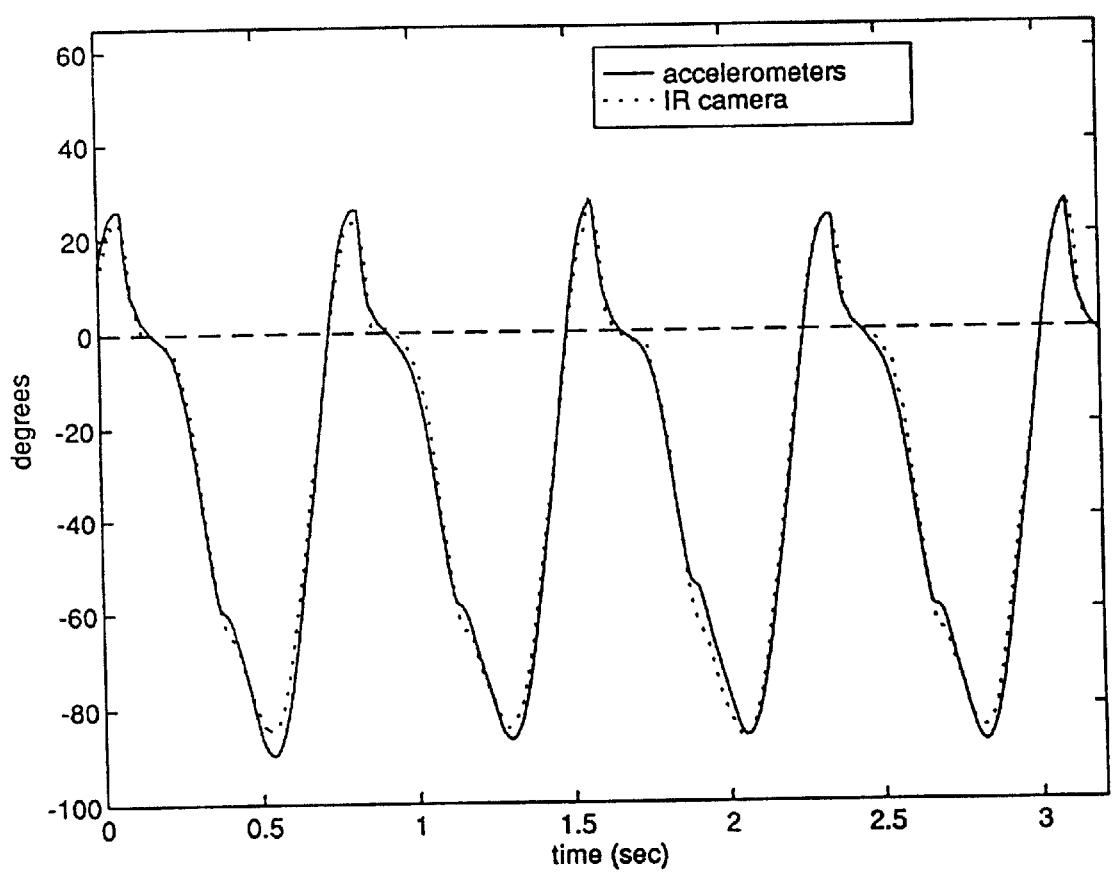
FIG. 7A illustrates the accuracy of determined foot angle over time.

FIG. 7A shows the foot angle θ that results from the zeroing and integrating method on the data from FIG. 6A$a$ (the zeroing and integrating is applied twice; once in the conversion of α and ω and once again in going from ω to θ). It is seen that it compares well with the independent θ from the infrared camera system that was used to film the subject.

When the accelerometers are stationary and in a preferred configuration (ie. on the heel or on the laces), the indicated signal levels of the accelerometers can be adjusted to zero. This will correct for temperature drift and individual sensor biases.

When the sensor cluster is attached at some other angle on the shoe, the indicated sensor angle in this orientation is used as a reference shoe angle that is used in conjunction with foot angle reset. In particular, instead of resetting the foot angle to zero on every foot strike, as is done in the heel mount position, the foot angle is set to the starting reference shoe angle for each new stride.

Foot Velocity

Components of the tangential and normal acceleration are preferably combined using the foot tilt angle θ to find the horizontal acceleration, $a_x$.

$$a_x = \frac{(a_{t_1} + a_{t_2})}{2}\cos(\theta) - a_n\sin(\theta)$$

Figure 8A:
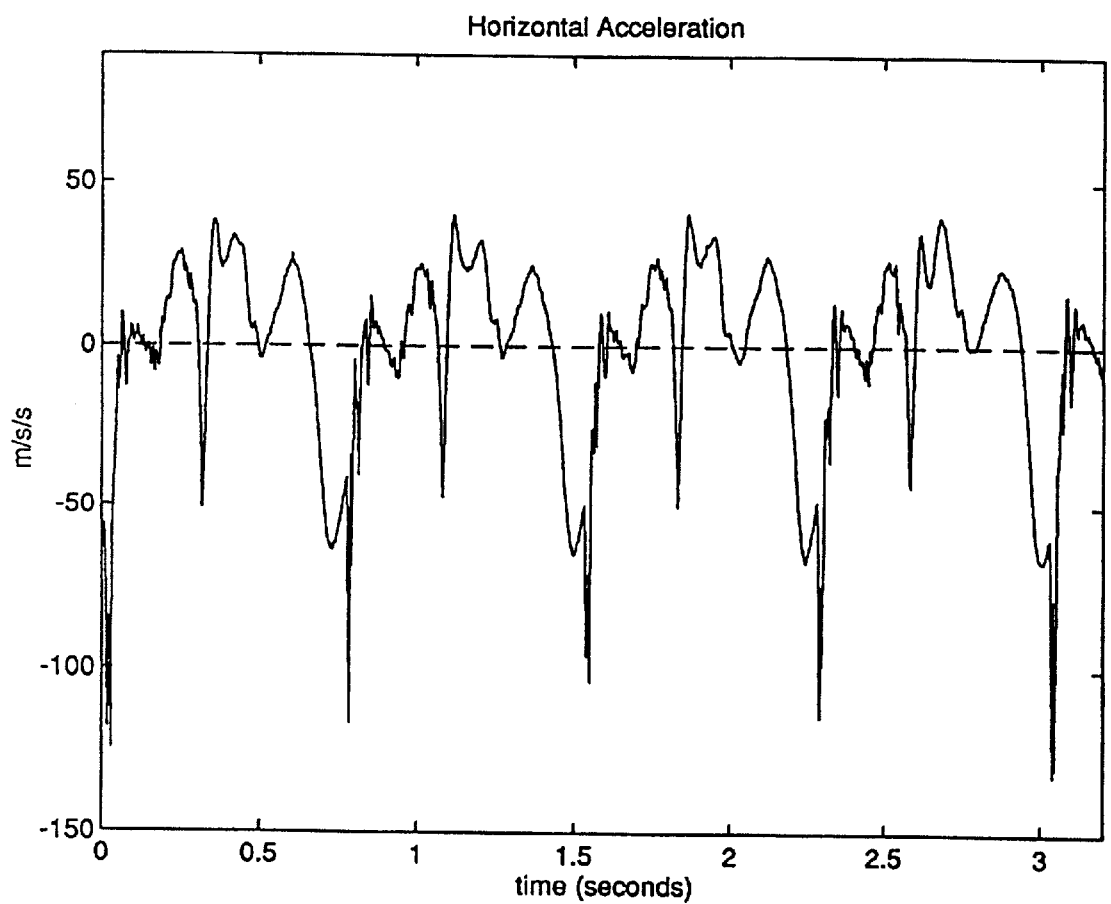
FIG. 8A is a plot of horizontal acceleration versus time.
Figure 9A:
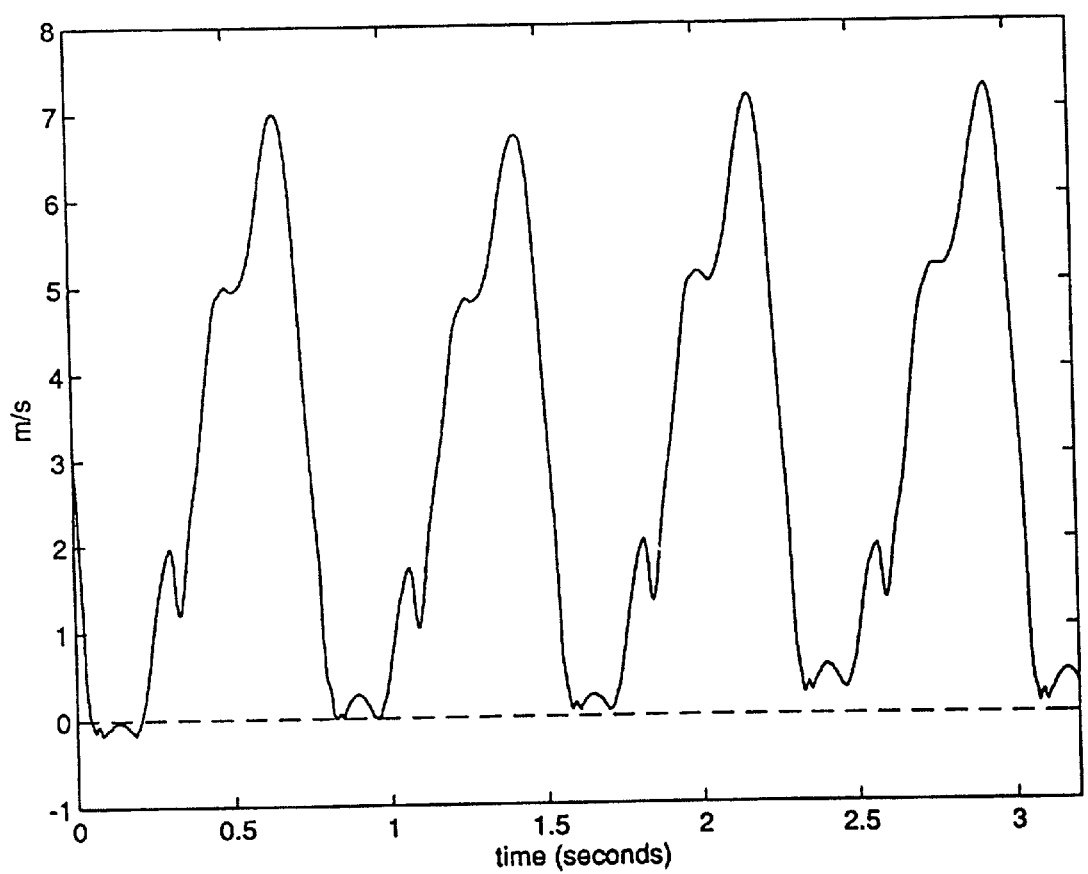
FIG. 9A is a plot of drifting velocity versus time.
Figure 10A:
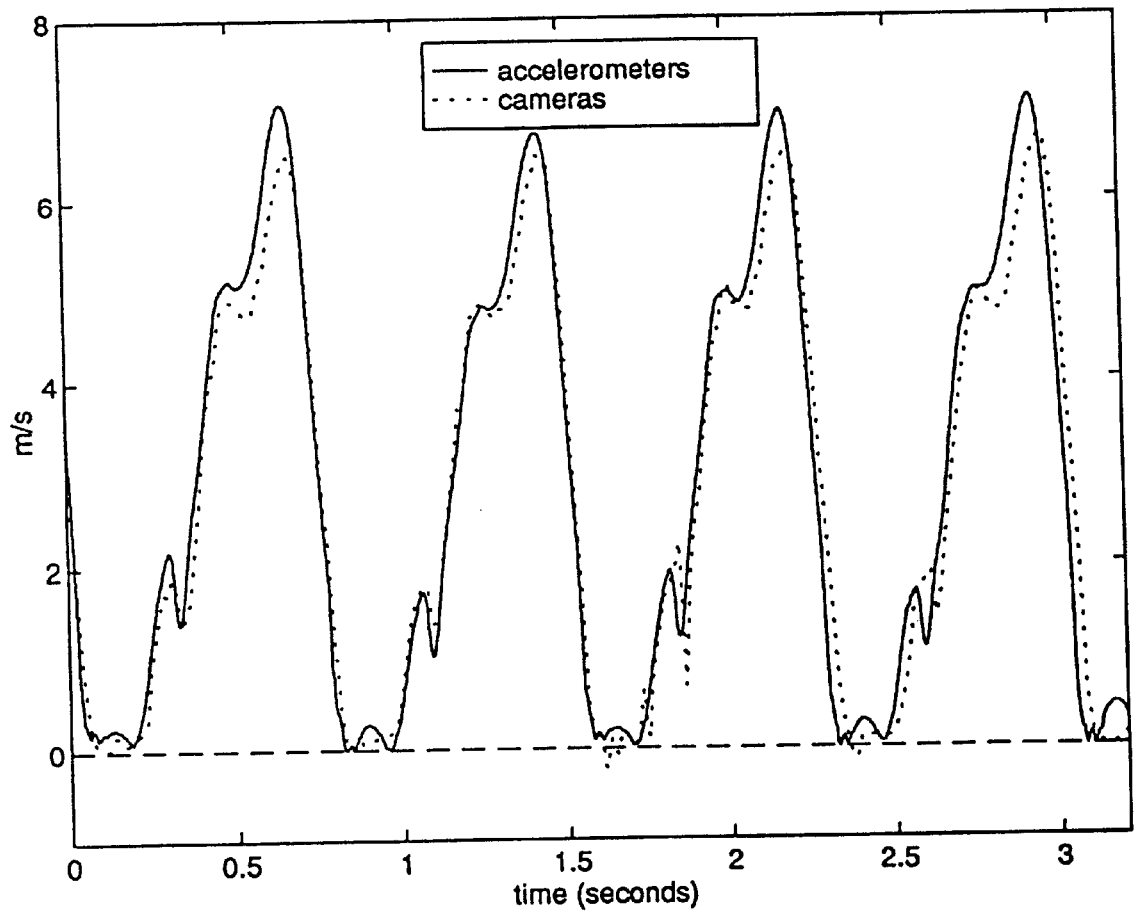
FIG. 10A is a plot of foot velocity versus time.

From the measured acceleration data in FIG. 4A and the calculated foot angle shown in FIG. 7A, the resulting horizontal acceleration is shown in FIG. 8A. An integration of $a_x$, yields velocity $v_x$ parallel to plane 100 (or with appropriate changes any other selected direction) as a function of time, as shown in FIG. 9A. It is seen that this signal also has low frequency drift. To correct the drift, zero offset was removed from the net horizontal acceleration since the horizontal velocity is zero at the beginning and end of each cycle. FIG. 10A compares the velocities computed from the camera system and the velocities from using the zeroing and integrating algorithm on the acceleration data. Excellent agreement is seen in the form of the two curves. The final mean velocities agree to within a few percent.

A further improvement in results is usually achieved by using the assumption that the minimum foot velocity is zero. This suggests that if any part of the entire velocity curve dips below zero there has been some small error somewhere. If the error has not corrupted the shape of the curve, it can be corrected by simply shifting the entire curve up so that the new minimum is exactly zero.

Generally, when the two parallel accelerometers are used to determine α, it is preferred to use the average of these two measurements to determine the mean, in this example the mean tangential acceleration, as indicated at 350 and generate a mean velocity as indicated by steps 34, 35, 36, and 38 described above and also shown in FIG. 15A.

Results using the Preferred Embodiment

Figure 11A:
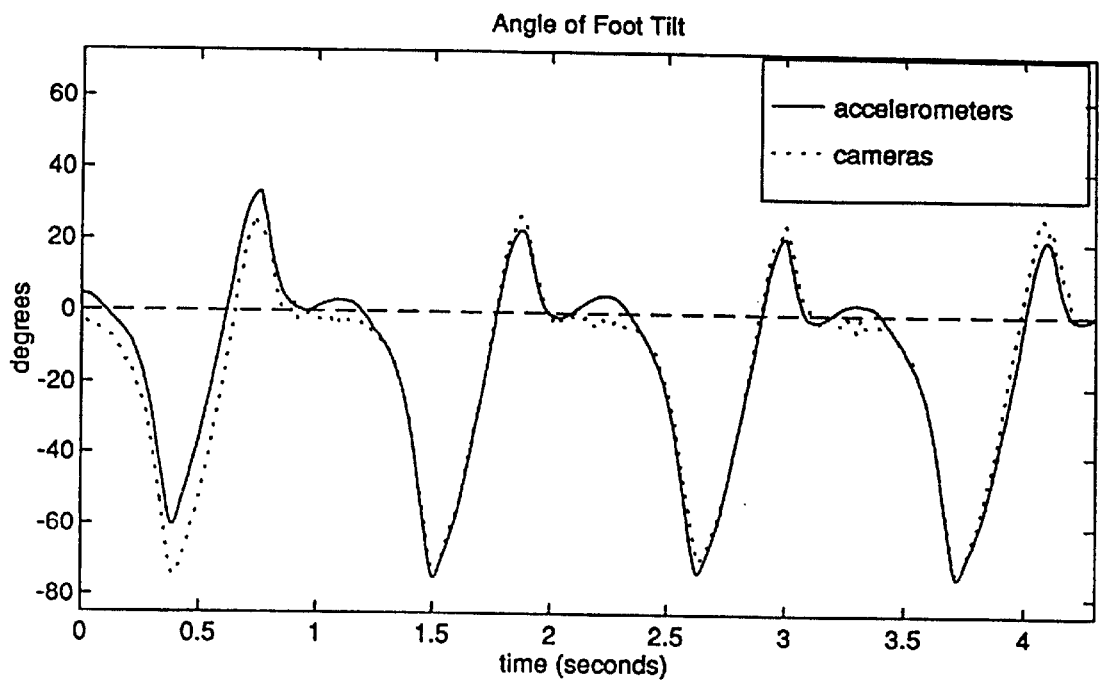
FIGS. 11A and 13A are plots of angle of foot tilt versus time.
Figure 12A:
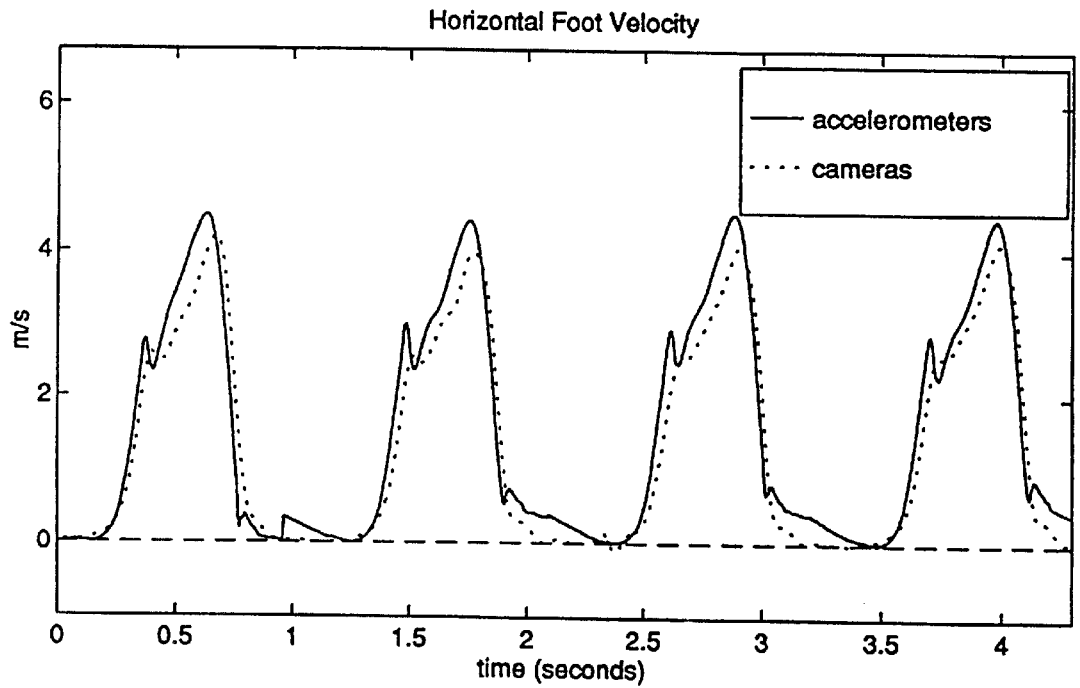
FIGS. 12A and 14A are plots of horizontal foot velocity versus time.
Figure 13A:
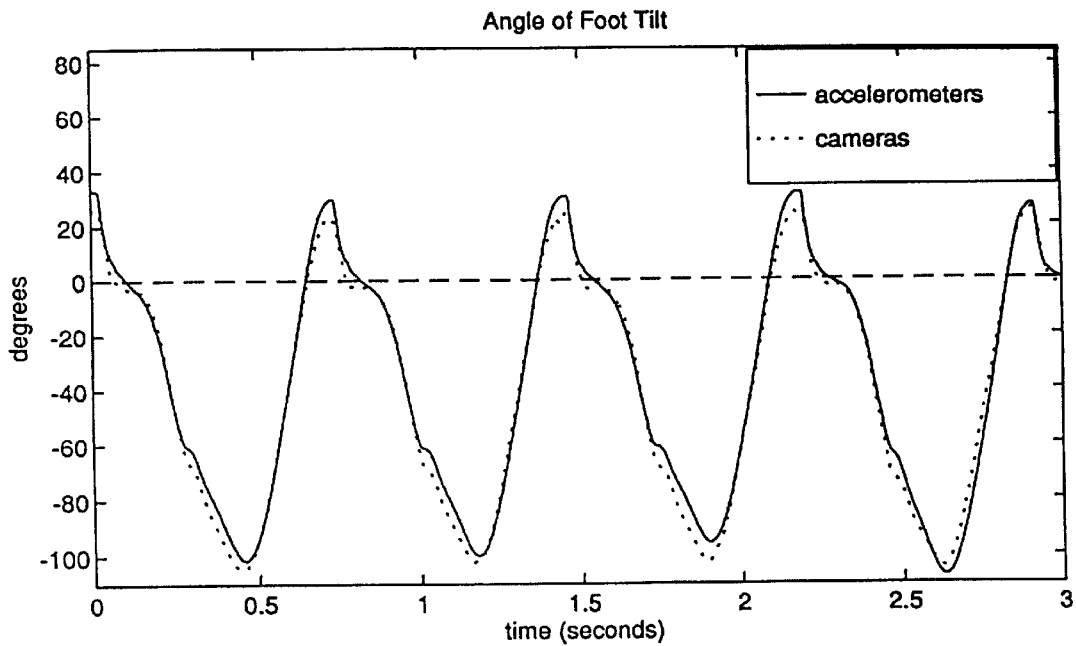
Figure 14A:
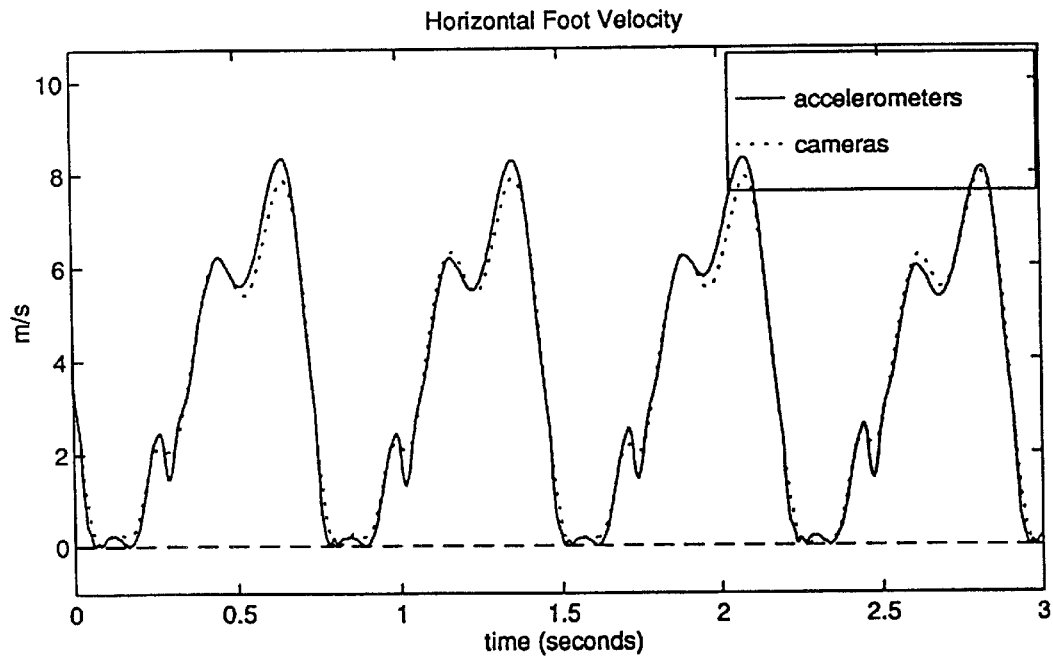

For the sake of coherence, all of the figures that have been shown so far have been of the same trial, a 3 m/s jog. FIGS. 11A and 12A show the critical parameters, namely the foot angle, θ, and foot velocity, $v_x$, for a 1.3 m/s walk, while FIGS. 13A and 14A show the same for a 3.8 nm/s run respectively. In these figures, the calculated values from the method described herein are compared to video camera analysis of the same parameters. It is observed that there is excellent overall agreement between the foot angle and foot velocity for these cases.

Figure 16A:
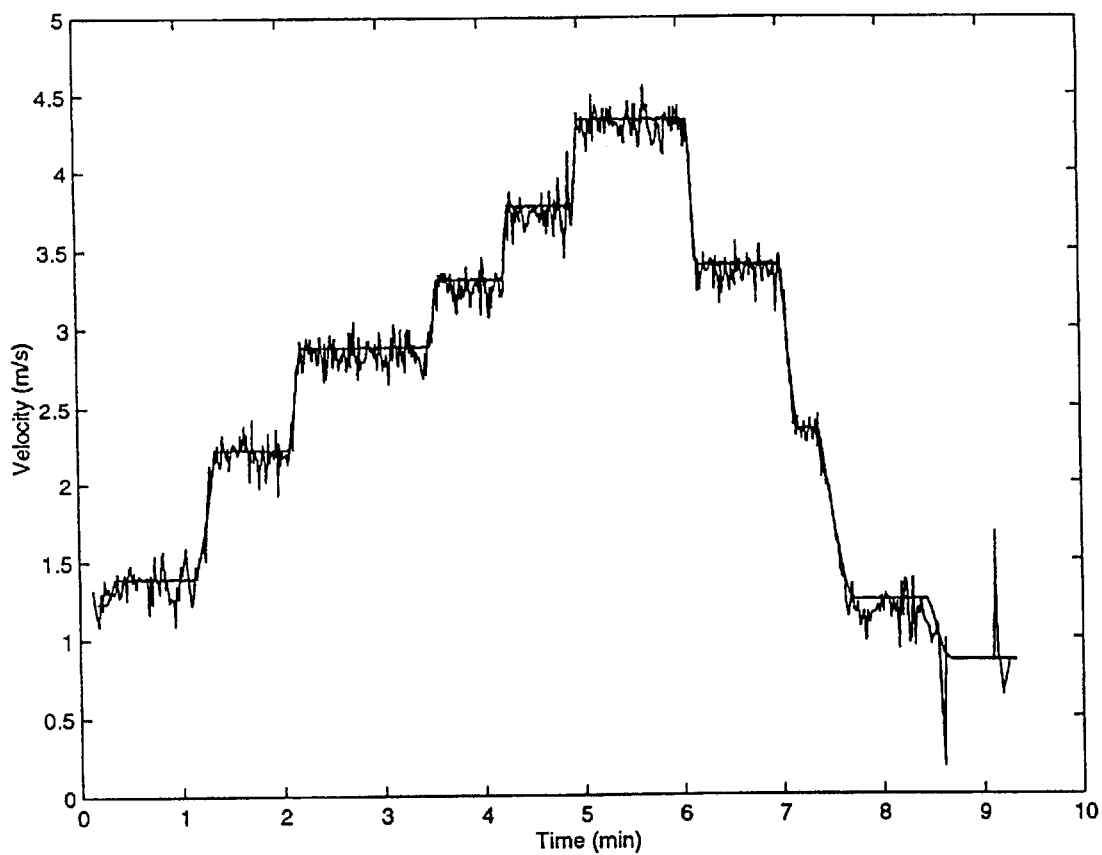
FIG. 16A is a plot of velocity versus time showing correlation of the invention at different stride velocities.

FIG. 16A shows a controlled experiment where the speed of a treadmill was selectively increased and the jogging speed of the runner measured using the present invention. The stopped line shows treadmill speed while the other plot is the results using the present invention. It is apparent that the results obtained using the present invention correlate very well with the actual speeds of the treadmill.

Gait Kinematics for Off-Angled Feet

The device and method described hereinbefore in this section assumes that during normal gait a subject's leg primarily swings through a plane parallel to that subject's sagittal plane. For ease of reference, the plane parallel is defined herein as the sagittal plane. While this assumption works well for most subjects, in some the foot is not aligned in this plane during all or a portion of leg swing. Thus, although the foot moves through the desired plane, the foot is off-angled either inwardly (sometimes called medially rotated or "pigeon-toed") or outwardly of the sagittal plane (sometimes called laterally rotated or "duck walk"). These foot alignments will cause an error in the measurements of the accelerometers. In particular, the accelerometers will only measure a portion of the actual acceleration and, therefore, the measured acceleration will be less than the actual acceleration.

Figure 3B:
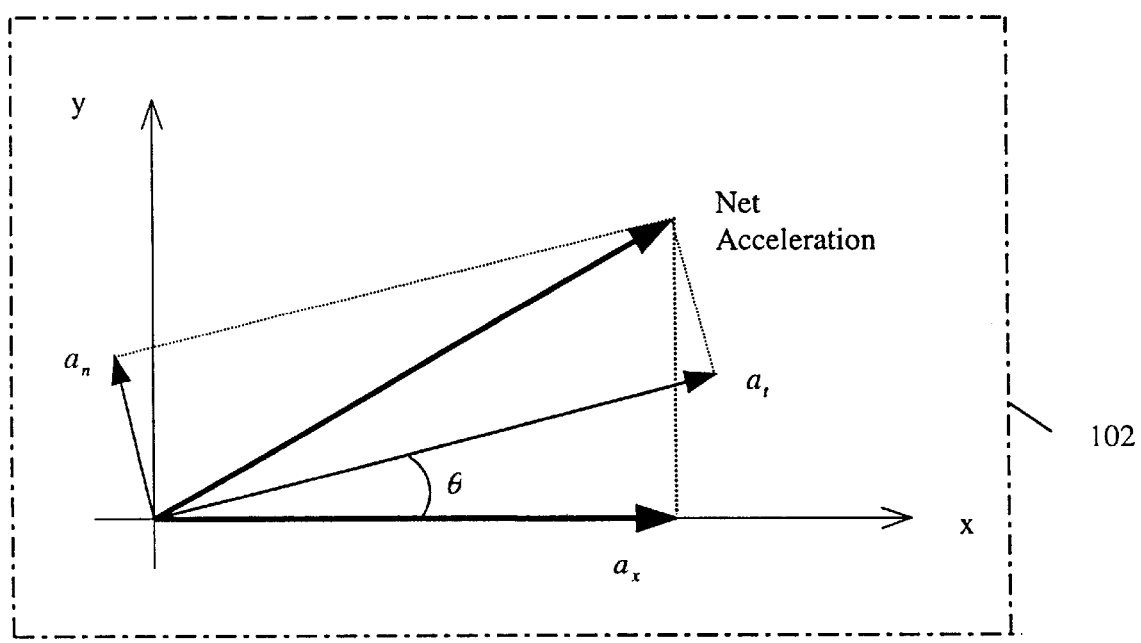
Figure 17A:
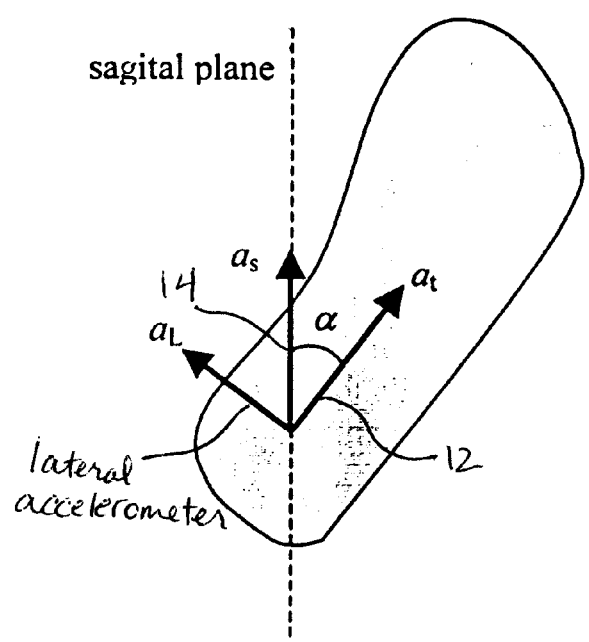
FIG. 17A illustrates the determination of acceleration in a plane parallel to the sagittal plane.

To correct for the problem of off-angled feet, an additional accelerometer can be used, termed herein as the lateral accelerometer, which measures in a direction that is out of the plane of motion and, preferably, substantially perpendicular to the accelerometers currently used (12 and 14 in FIG. 2). With reference to FIG. 3b, the lateral accelerometer would be aligned in the z-direction. Referring to FIG. 17A, the acceleration derived from the lateral accelerometer is, $a_L$. If we consider a plan view of the shoe in movement through the sagittal plane where:

$a_t$=tangential acceleration
$a_L$=lateral acceleration
$a_s$=sagittal plane acceleration
α=angle from sagittal plane.

The acceleration in the sagittal plane, $a_s$ can be computed from $$a_s = \sqrt{a_t^2 + a_L^2}$$

The value of the sagittal acceleration (positive or negative) can be determined from the sign of $a_t$. The angle, α, can be found from $$\alpha = \tan^{-1}\left(\frac{a_L}{a_t}\right)$$

Both of these quantities are computed for each time step. The sagittal acceleration in this model is treated as the tangential acceleration in the 2-D model and can by used with the normal acceleration to determine further gait kinematic results. In an alternate embodiment, the normal acceleration can be combined with the lateral acceleration first and then combined with the tangential acceleration.

Pronation

Figure 18A:
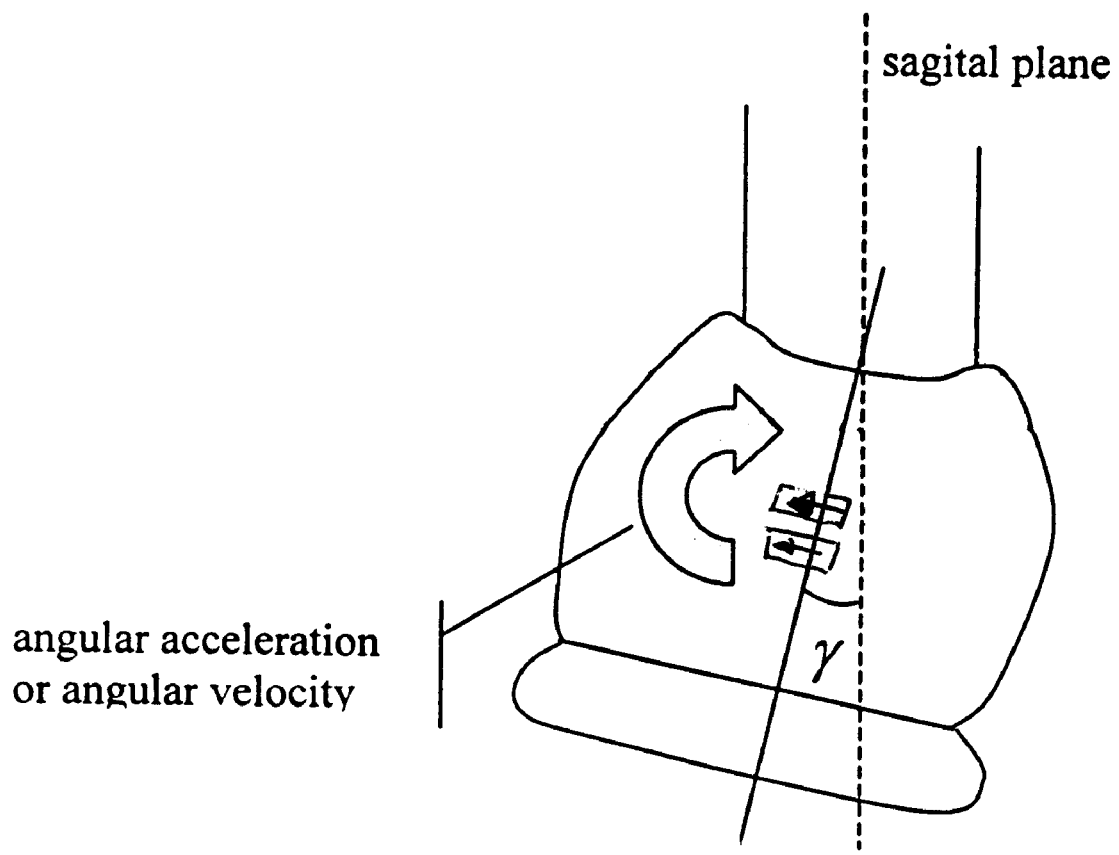
FIG. 18A illustrates the foot pronation angle for a person.

A device according to the present invention is useful for determining the degree of pronation in a person's gait. Referring to FIG. 18A, a person's foot sometimes rolls when viewed from the front or rear. This is termed pronation. In assessing the degree of pronation of a person, the angle γ between a plane parallel to the sagittal plane and the angular orientation of a person's foot is measured. To be able to measure this angle, the angular acceleration in this transverse plane can be recorded and then double integrated. This angular acceleration can be measured using a pair of parallel spaced accelerometers positioned to record acceleration in a plane perpendicular to the sagittal plane.

Alternately, the angular acceleration can be determined by a dedicated angular accelerometer.

Alternatively, an angular rate sensor could be used to measure angular velocity and this signal could be integrated to indicate the desired angle, γ. Alternatively, a direct means of angle measurement could alternately be used for this purpose.

Drift may be present in the signal. This drift can be removed by resetting the angle γ at each foot impact. Where the determination of an absolute angle measurement is not required, resetting pronation foot angle γ may not be necessary. In this case, it may be desirable to obtain an indication of the amplitude of the roll angle by noting the minimum and maximum roll angles during each stride.

Impact Force Analysis

Many running injuries are caused from excessive forces imparted to the body during the foot-strike portion of the gait. This includes shin splints, stress fractures and various joint problems. When a person has these problems, it is often suggested that it is something in their running style (stride length, heel vs. mid-strike landing), current running shoes or running surface that is the culprit. Remedies are suggested and sometimes temporary success is found, only to return again. The difficulty with this type of problem is in its diagnosis and, in particular, how to determine which of these potential contributing factors is the problem. There are no low-cost measurement tools to determine the impact forces.

It is well known that force and acceleration are directly related to each other from Newton's first law F=ma In a method according to the present invention, all necessary information is available to determine the acceleration of interest.

To compare impact forces over a variety of scenarios, it is not necessary to have an absolute force measurement, but instead a relative force measurement will suffice. In particular, if it is determined that one uncalibrated force is some level, F0, one can observe how this level changes with any of the various factors (stride length, landing position, running shoes, surface, length of run, etc).

This method permits a runner, for example, to test out various running styles, running shoes and running surfaces and be able to determine in real time which factor most largely affects the impact forces.

Summary

It will be apparent that the invention may be used for many applications other than those described above including general kinematic measurements in one, two or three dimensions depending on the number and position of the accelerometers and angle measurement devices. Thus the invention may be used in robotic controls, linkage and trajectory analysis, for example. Clearly, the invention finds specific application in the biomedical field in prosthetics and as gait speedometers for walkers, runners or other athletes. Note that the use of this device is not limited to human applications.

A primary advantage of the described invention, is that all calculated gait parameters are available as a function of time. This opens up a wide range of real-time post-processing possibilities for use in scientific analysis and control operations.

While the disclosure has described the accelerometers, etc. mounted on the counter of the shoe 10 they may be mounted at any appropriate location in fixed relation to the datum plane defining surface 11 or other such means. For example, they could be mounted to the shoe laces, pinned to the side of the shoe, built into the sole of the shoe or strapped to the foot.

Having described the invention, modifications will be evident to those skilled in the art without departing from the spirit of the invention as described above.

The embodiments of the invention in which an exclusive property or privilege is claimed are defined as follows:

1. A method of determining gait kinematics for a subject in each of a plurality of strides comprised during each stride defining a fresh datum plane, determining angles between a pair of accelerometers and said datum plane, said pair of accelerometers being adapted to measure acceleration in two directions, the two directions being separated by a known angle of greater than 0°, and being adapted to measure acceleration in a plane of motion substantially perpendicular to said datum plane, measuring acceleration in said plane of motion in said two directions, converting said accelerations to provide determination of a gait kinematic result for each said stride.

2. The method as defined in claim 1 wherein the two directions are substantially mutually perpendicular.

3. The method as defined in claim 1 wherein the gait kinematic result is selected from the group consisting of acceleration in a selected direction, velocity in a selected direction or distance in a selected direction.

4. The method as defined in claim 3 wherein acceleration, velocity or distance is measured in a direction that is parallel to the datum plane and in the plane of motion.

5. The method as defined in claim 3 wherein acceleration, velocity or distance is measured in a direction that is parallel to the datum plane and in said plane of motion.

6. The method as defined in claim 3 further comprising integrating the acceleration in a selected direction to determine velocity in a selected direction.

7. The method as defined in claim 3 further comprising integrating velocity in a selected direction to define distance traveled in a selected direction.

8. The method as defined in claim 1 wherein the fresh datum plane is preferably defined when the pair of accelerometers are at a selected position relative to the datum plane.

9. The method as defined in claim 8 wherein the pair of accelerometers are in the selected position as indicated by foot impact with a surface just prior to a stance phase of the gait.

10. The method as defined in claim 9 wherein the fresh datum plane is defined at foot impact plus 0.1 seconds.

11. The method of claim 1 wherein the gait kinematic result is horizontal acceleration and the method further comprising integrating said horizontal acceleration to define stride velocity.

12. The method of claim 1 wherein the gait kinematic result is velocity in a selected direction and the method further comprises integrating said velocity in a selected direction to define distance in said selected direction.

13. The method as defined in claim 1 further comprising adjusting for drift error correction.

14. The method as defined in claim 1 further comprising determining the subject's mass and using the mass to determine impact force.

15. The method as defined in claim 1 further comprising measuring acceleration in a lateral direction out of the plane of motion and converting said accelerations measured by the pair of accelerometers and the lateral accelerometer to provide acceleration in a selected direction.

16. The method as defined in claim 15 wherein the lateral direction is substantially perpendicular to each of the pair of accelerometers.

17. A device for measuring gait kinematics comprising means for mounting a pair of accelerometers in a fixed relationship to a datum plane defining surface, said pair of accelerometers being adapted to measure acceleration in two directions, the two directions being separated by a known angle of greater than 0°, means defining a datum plane for each stride for which said gait kinematics is measured as a plane occupied by said datum plane defining surface when said datum plane defining surface is in a stationary position in a stance phase of said stride, means for determining angular orientation of said accelerometers to said datum plane, means for determining a gait kinematic result based on measurements of acceleration by said pair of accelerometers and said determined angular orientation of said accelerometers to said datum plane.

18. The device of claim 17 wherein the two directions are substantially mutually perpendicular.

19. The device of claim 17 wherein the gait kinematic result is selected from the group consisting of acceleration in a selected direction, velocity in a selected direction or distance in a selected direction.

20. The device of claim 19 wherein acceleration, velocity or distance is measured in a direction that is parallel to the datum plane and in said plane of motion.

21. The device of claim 17 further comprising a means for adjusting for drift error correction.

22. The device of claim 17 wherein the means for determining angular orientation of said accelerometers to said datum plane comprises of a pair of spaced substantially parallel accelerometers mounted in fixed relation to said datum plane defining surface and means for calculating angular orientation based on differences in accelerations measured by said pair of spaced substantially parallel accelerometers.

23. The device of claim 17 wherein the pair of accelerometers is adapted to measure the acceleration in a plane of motion, and the device further comprising a lateral accelerometer mounted in a fixed, known and mutually perpendicular relationship to the pair of accelerometers and adapted to measure acceleration in a third direction selected to be out of the plane of motion.

24. The device of claim 23 wherein the lateral accelerometer is substantially perpendicular to the pair of accelerometers.

25. A method of determining gait kinematics comprised during each stride defining a datum plane, determining angles between a pair of accelerometers and said datum plane, said pair of accelerometers being adapted to measure acceleration in two directions, the two directions being separated by a known angle of greater than 0° and being adapted to measure acceleration in a plane of motion substantially perpendicular to said datum plane, measuring acceleration in said plane of motion in said two directions, converting said accelerations to provide determination of a gait kinematic result for each said stride and adjusting for drift error correction in said gait kinematic result.

26. The method of claim 25 wherein the pair of accelerometers are substantially mutually perpendicular.

27. The method of claim 25 wherein the gait kinematic result is selected from the group consisting of acceleration in a selected direction, velocity in a selected direction or distance in a selected direction.

28. The method of claim 25 wherein the adjusting step is made prior to the step of converting to provide the gait kinematic result.

29. The method of claim 25 wherein the adjusting step is conducted after the step of converting to provide the gait kinematic result.

30. The method of claim 25 wherein the step of adjusting includes employing known limitations in the gait kinematic result.

31. The method of claim 30 wherein any velocity in a selected direction results are adjusted to remove any negative velocity results therefrom.

32. The method of claim 25 further comprising an integration step to derive further gait kinematic results from the gait kinematic result and adjusting for drift error correction in the integration step.

33. The method of claim 25 wherein the gait kinematic result is acceleration in said selected direction and the method further comprises integrating the acceleration in a selected direction to define velocity in said selected direction.

34. The method of claim 33 further comprising determining a mean acceleration in said selected direction and removing the mean acceleration from the acceleration in said selected direction prior to integrating to determine velocity in said selected direction.

35. The method of claim 34 wherein the determination and removal of the mean acceleration from the acceleration in said selected direction is conducted for each of a plurality of strides.

36. The method of claim 34 wherein the mean acceleration in a selected direction is obtained from a previously determined gait kinematic result.

37. The method of claim 25 wherein the gait kinematic result is velocity in a selected direction and the method further comprises integrating said velocity in a selected direction to define distance traveled in a selected direction.

38. The method of claim 37 further comprising determining a mean velocity in said selected direction and removing the mean velocity from the velocity in said selected direction prior to integrating to determine distance traveled in a selected direction.

39. The method of claim 25 wherein the gait kinematic result is horizontal acceleration and the method further comprising integrating said horizontal acceleration to define stride velocity.

40. The method of claim 39 further comprising determining a mean horizontal acceleration and removing the mean horizontal acceleration from the horizontal acceleration prior to integrating to determine stride velocity.

41. A device for measuring gait kinematics comprising means for mounting a pair of accelerometers in a fixed relationship to a datum plane defining surface and said pair of accelerometers being adapted to measure acceleration in two directions, the two directions being separated by a known angle of greater than 0°, means defining a datum plane measured as a plane occupied by said datum plane defining surface when said datum plane defining surface is in a stationary position in a stance phase of said stride, means for determining angular orientation of said accelerometers to said datum plane, means for determining a gait kinematic result based on measurements of acceleration by said pair of accelerometers and said determined angular orientation of said accelerometers to said datum plane and means for adjusting for drift error correction.

42. The device of claim 41 wherein the two directions are substantially mutually perpendicular.

43. The device of claim 41 wherein the gait kinematic result is selected from the group consisting of acceleration in a selected direction, velocity in a selected direction or distance in a selected direction.

44. The device of claim 41 wherein acceleration, velocity or distance is in a direction that is parallel to the datum plane and in said plane of motion.

45. The device of claim 41 wherein the means for adjusting for drift error correction is a system for determining the mean signal of any particular gait signal and applying a mean signal to the particular signal prior to integration to determine further gait kinematic results.

46. The device of claim 41 wherein the means for adjusting for drift error correction is a system for using known physical limits of a derived signal to account for drift.

47. A device for measuring gait kinematics of a stride in a subject having a foot, the device comprising means for mounting a pair of accelerometers in a fixed relationship to a datum plane defining surface, said pair of accelerometers being adapted to measure acceleration in two substantially parallel directions about an axis of rotation defined by movement of the foot, means defining a datum plane measured as a plane occupied by said datum plane defining surface when said datum plane defining surface is in a stationary position in a stance phase of said stride, and means for calculating angular orientation based on differences in accelerations measured by said pair of accelerometers.

48. The device of claim 47 wherein the axis of the foot is substantially parallel to a sagittal plane defined by the subject and with the datum plane defining surface.

49. The device of claim 47 wherein the axis of rotation is that about which is defined pronation.

50. A method of determining pronation characteristics of a foot during a stride comprising during each stride defining a datum plane, determining angular acceleration about an axis about which a foot pronates, converting the angular acceleration relative to the datum plane to determine an angle of pronation for the foot.

\* \* \* \* \*